US011058549B2

(12) United States Patent
Zellmer et al.

(10) Patent No.: US 11,058,549 B2
(45) Date of Patent: Jul. 13, 2021

(54) SYSTEM AND METHOD FOR DYNAMICALLY STIMULATING BONE GROWTH

(71) Applicant: Intelligent Implants Limited, Cork (IE)

(72) Inventors: Erik Zellmer, St. Louis, MO (US); Rory Murphy, St. Louis, MO (US)

(73) Assignee: Intelligent Implants Limited, Cork (IE)

( * ) Notice: Subject to any disclaimer, the term of this patent is extended or adjusted under 35 U.S.C. 154(b) by 0 days.

(21) Appl. No.: 16/206,905

(22) Filed: Nov. 30, 2018

(65) Prior Publication Data
US 2019/0247198 A1 Aug. 15, 2019

Related U.S. Application Data

(62) Division of application No. 15/075,152, filed on Mar. 19, 2016, now Pat. No. 10,292,831.
(Continued)

(51) Int. Cl.
*A61F 2/44* (2006.01)
*A61N 1/32* (2006.01)
(Continued)

(52) U.S. Cl.
CPC .......... *A61F 2/4455* (2013.01); *A61B 5/0538* (2013.01); *A61B 5/4504* (2013.01); *A61B 5/4566* (2013.01); *A61B 5/7225* (2013.01); *A61F 2/28* (2013.01); *A61F 2/44* (2013.01); *A61F 2/4465* (2013.01); *A61N 1/326* (2013.01); *A61N 1/3787* (2013.01); *A61B 5/0031* (2013.01); *A61B 5/686* (2013.01);
(Continued)

(58) Field of Classification Search
CPC .......... A61F 2/44; A61F 2/4455; A61N 1/326
See application file for complete search history.

(56) References Cited

U.S. PATENT DOCUMENTS 3,842,841 A * 10/1974 Brighton ................ A61B 17/58
607/52
4,313,438 A 2/1982 Greatbatch
(Continued)

FOREIGN PATENT DOCUMENTS

WO 2013188380 A1 12/2013
WO 2014089299 A3 10/2014

OTHER PUBLICATIONS

Laughner JI, et al. (2013) A Fully Implantable Pacemaker for the Mouse: From Battery to Wireless Power. PLOS ONE 8(10): e76291. https://doi.org/10.1371/journal.pone.0076291, Oct. 23, 2013.
(Continued)

*Primary Examiner* — Nicholas W Woodall
(74) *Attorney, Agent, or Firm* — Alpine Patents LLC; Brian Van Osdol

(57) ABSTRACT

A system and method for electrical stimulation in an orthopedic implant that includes at least one implantable component with an implant body, a plurality of electrodes, and implant circuitry is effective to convert an external wireless power transmission to an electrical current and effective to control the plurality of electrodes; and at least one non-implant with a power source, and transmitter circuitry to generate the electromagnetic field that couples with the implant circuitry.

15 Claims, 34 Drawing Sheets

Related U.S. Application Data

(60) Provisional application No. 62/135,769, filed on Mar. 20, 2015.

(51) Int. Cl.
*A61F 2/28* (2006.01)
*A61B 5/00* (2006.01)
*A61B 5/0538* (2021.01)
*A61N 1/378* (2006.01)
*A61F 2/30* (2006.01)
*A61F 2/48* (2006.01)
*A61F 2/46* (2006.01)

(52) U.S. Cl.
CPC ............... *A61B 2562/0219* (2013.01); *A61F 2002/2821* (2013.01); *A61F 2002/3067* (2013.01); *A61F 2002/30187* (2013.01); *A61F 2002/30593* (2013.01); *A61F 2002/30622* (2013.01); *A61F 2002/30668* (2013.01); *A61F 2002/469* (2013.01); *A61F 2002/482* (2013.01)

(56) References Cited

U.S. PATENT DOCUMENTS

| | | | |
|---|---|---|---|
| 4,690,144 A | 9/1987 | Rise et al. | |
| 4,690,166 A | 9/1987 | Howeth | |
| 5,565,005 A * | 10/1996 | Erickson | A61N 1/05 607/51 |
| 5,974,342 A | 10/1999 | Petrofsky | |
| 5,989,289 A | 11/1999 | Coates et al. | |
| 6,120,502 A | 9/2000 | Michelson | |
| 6,292,699 B1 | 9/2001 | Simon et al. | |
| 6,400,990 B1 | 6/2002 | Silvian | |
| 6,582,467 B1 | 6/2003 | Teitelbaum et al. | |
| 6,605,089 B1 | 8/2003 | Michelson | |
| 7,104,986 B2 | 9/2006 | Hovda et al. | |
| 7,309,338 B2 | 12/2007 | Cragg | |
| 7,324,852 B2 | 1/2008 | Barolat et al. | |
| 7,359,755 B2 | 4/2008 | Jones et al. | |
| 7,455,672 B2 | 11/2008 | Michelson | |
| 7,578,819 B2 | 8/2009 | Bleich et al. | |
| 7,935,116 B2 | 5/2011 | Michelson | |
| 8,014,873 B2 | 9/2011 | Jones et al. | |
| 8,078,282 B2 | 12/2011 | Nycz | |
| 8,078,283 B2 * | 12/2011 | Cowan | A61N 1/3604 607/51 |
| 8,206,387 B2 | 6/2012 | Michelson | |
| 8,463,401 B2 | 6/2013 | Jones et al. | |
| 8,740,879 B2 | 6/2014 | Martinson et al. | |
| 8,771,360 B2 | 7/2014 | Jimenez et al. | |
| 8,838,249 B2 * | 9/2014 | Nycz | A61N 1/205 607/51 |
| 8,903,502 B2 | 12/2014 | Perryman et al. | |
| 2003/0078634 A1 | 4/2003 | Schulman et al. | |
| 2005/0033393 A1 | 2/2005 | Daglow | |
| 2007/0250045 A1 | 10/2007 | Trieu | |
| 2008/0294211 A1 | 11/2008 | Moffitt | |
| 2008/0300660 A1 | 12/2008 | John | |
| 2009/0062886 A1 | 3/2009 | O'Handley et al. | |
| 2011/0092948 A1 | 4/2011 | Shachar et al. | |
| 2013/0150970 A1 | 6/2013 | Thaiyananthan | |
| 2013/0296940 A1 | 11/2013 | Northcutt et al. | |
| 2014/0114382 A1 | 4/2014 | Kim | |
| 2014/0275847 A1 | 9/2014 | Perryman et al. | |
| 2014/0277260 A1 | 9/2014 | Khalil et al. | |
| 2014/0371823 A1 * | 12/2014 | Mashiach | A61F 5/566 607/60 |
| 2015/0018728 A1 | 1/2015 | Gross et al. | |
| 2015/0134061 A1 | 5/2015 | Friis et al. | |
| 2017/0157407 A1 | 6/2017 | Zellmer et al. | |

OTHER PUBLICATIONS

WIPO European Searching Authority, "PCT2016000482 WO Search and Opinion", dated Jul. 7, 2016.

* cited by examiner

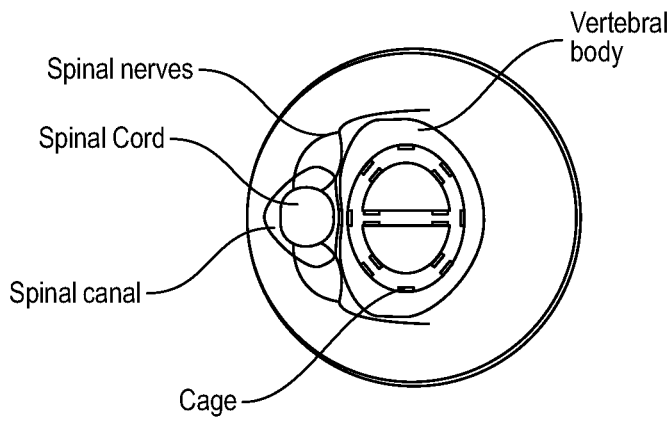
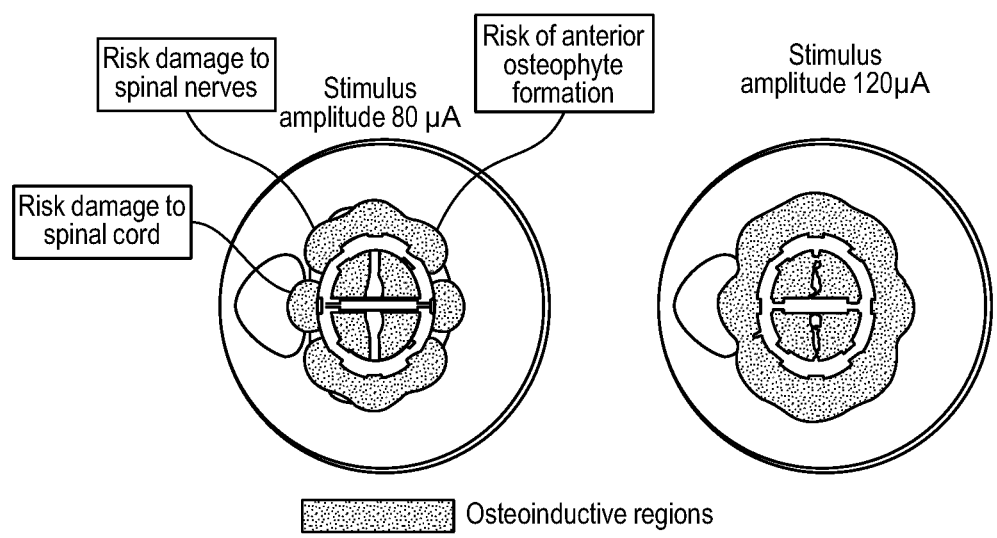
FIGURE 25

Guided osteoinduction, examples:

Managing mass formation in spinal canal
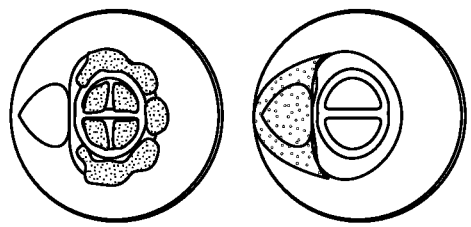

Managing mass formation in spinal canal and intervertebral formamen
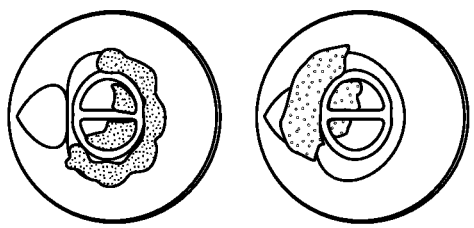

Managing unilateral anterior osteophytes
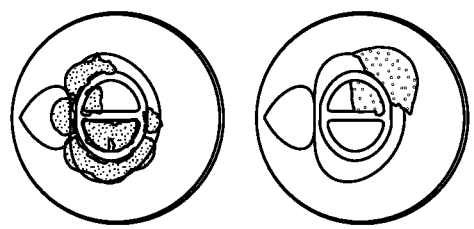

Managing unilateral anterior osteophytes and bilateral posterior osteophytes
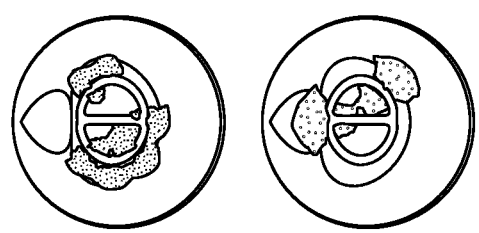

Increasing bone mass on one or both sides of the fusion space while maintaining bone mass in the front of the space avoiding the creation of anterior osteophytes
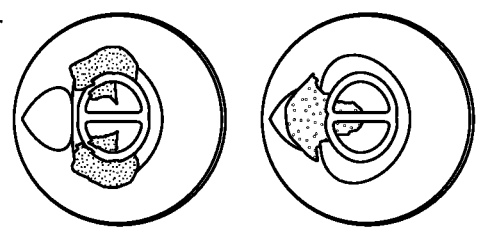

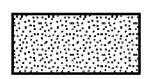 Osteoinductive regions  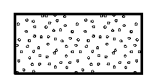 Osteolytic regions

FIGURE 26

Guided osteoinduction, examples:

Managing mass formation in spinal canal
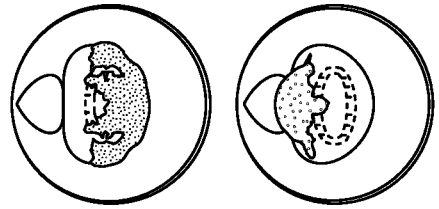

---

Managing mass formation in spinal canal and intervertebral formamen
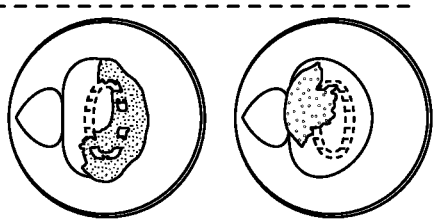

---

Managing unilateral anterior osteophytes
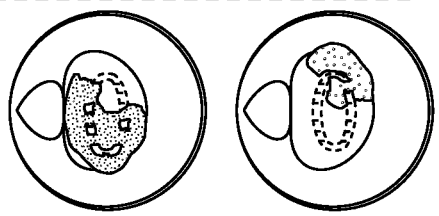

---

Managing unilateral anterior osteophytes and bilateral posterior osteophytes
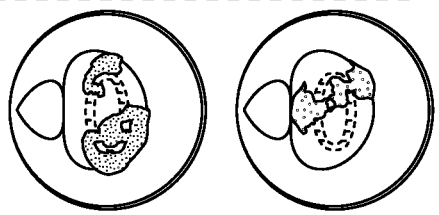

---

Increasing bone mass on one or both sides of the fusion space while maintaining bone mass in the front of the space avoiding the creation of anterior osteophytes
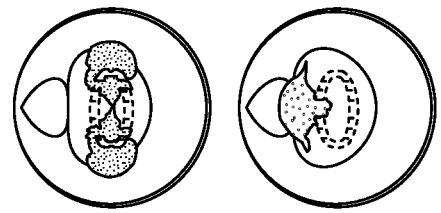

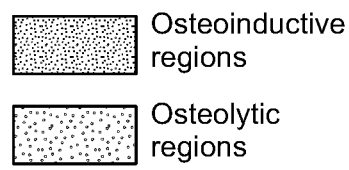

FIGURE 28A

Guided osteoinduction, examples:

Managing mass formation in spinal canal
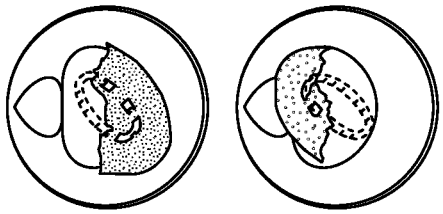

Managing mass formation in spinal canal and intervertebral formamen
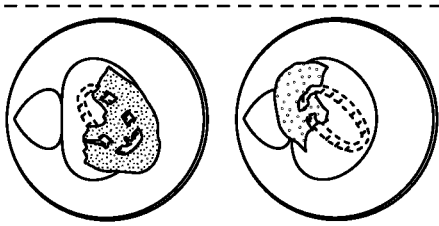

Managing unilateral anterior osteophytes
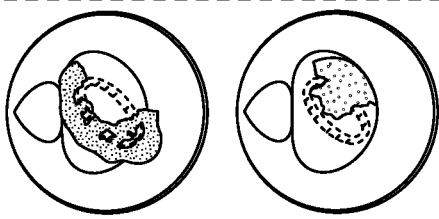

Managing unilateral anterior osteophytes and bilateral posterior osteophytes
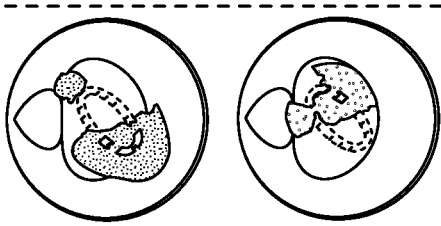

Increasing bone mass on one or both sides of the fusion space while maintaining bone mass in the front of the space avoiding the creation of anterior osteophytes
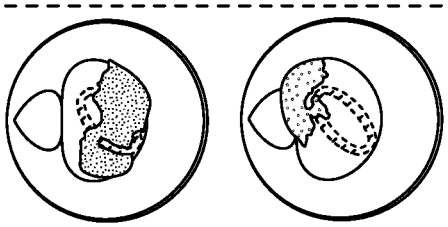

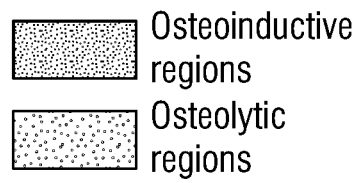
Osteoinductive regions
Osteolytic regions

FIGURE 28B

Guided osteoinduction, examples:

Managing mass formation in spinal canal
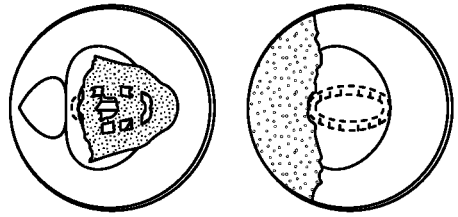

Managing mass formation in spinal canal and intervertebral formamen
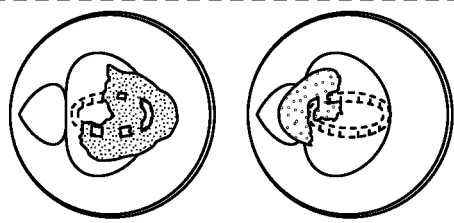

Managing unilateral anterior osteophytes
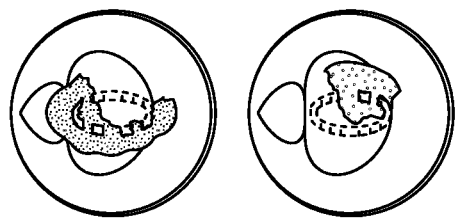

Managing unilateral anterior osteophytes and bilateral posterior osteophytes
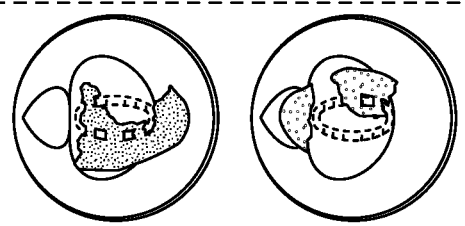

Increasing bone mass on one or both sides of the fusion space while maintaining bone mass in the front of the space avoiding the creation of anterior osteophytes
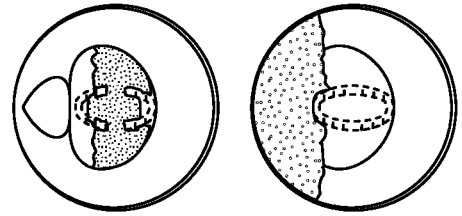

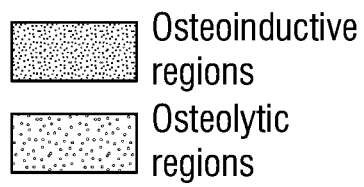
Osteoinductive regions
Osteolytic regions

FIGURE 28C

SYSTEM AND METHOD FOR DYNAMICALLY STIMULATING BONE GROWTH

CROSS-REFERENCE TO RELATED APPLICATIONS

This Application is a divisional application of U.S. patent application Ser. No. 15/075,152, filed on 19 Mar. 2016, which claims the benefit of U.S. Provisional Application No. 62/135,769, filed on 20 Mar. 2015, which is incorporated in its entirety by this reference.

TECHNICAL FIELD

This invention relates generally to the field of electrical stimulation following orthopedic operations, and more specifically to a new and useful system and method for dynamically stimulating bone growth.

BACKGROUND

Spinal fusion is one of the most commonly performed surgical procedures within the US and in Europe. The goal of spinal fusion surgery is to introduce bone growth between two or more vertebrae, fusing them into a single, continuous unit. Spinal fusion surgery is performed in the lumbar, cervical and thoracic regions, and fusions within each region are associated with a different set of complications. Even so, most complications following spinal fusion can be generalized into two broad categories: non-fusions, where the vertebrae are not fused into a singular unit due to insufficient bone formation within the fusion space; heterotopic ossification, where bone growth damages or impinges on tissue causing harm or discomfort to the patient. Examples of heterotopic ossification includes: Anterior osteophyte formation causing mass effect on the esophagus leading difficulty of swallowing (cervical fusions); ossification of the posterior longitudinal ligament; and formation of posterior osteophyte and/or other excessive posterior bone growth pressuring the spinal cord and/or spinal nerves.

Many contemporary spinal fusion hardware and biologics include designs to address the problems associated with non-unions, with little regard to heterotopic ossification. For example, commonly used biologics, particularly recombinant human bone morphogenetic protein (rhBMP-2), have been used to reduce non-fusion rates by increasing bone formation in the fusion space and the volume surrounding it. While clinically proven to decrease non-unions, numerous studies have shown that the biologic causes a host of side effects including but not limited to cancer, tissue swelling, growth of benign tissue, teratogenicity, pathological heterotopic ossification, nerve injury and spinal cord injury. While not all side effects caused by rhBMP-2 are related to heterotopic ossification, many are. As such, the biologic represents an illustrating example of how, nonspecific, unguided osteoinduction can be harmful to a patient and the delicate balance between increasing fusion rates and avoiding heterotopic ossification.

A second method utilized in reducing non-union rates is electrical stimulation. When mechanical stress is exerted on bone, an electric field is created. In the body, this electrical field constitutes a signal causing a physiological response resulting in osteoinduction or osteolysis. Consequently, it is possible to cause osteoinduction or osteolysis by introducing an electrical field in the volume within and surrounding a segment of bone. In volumes where the current density is above a certain threshold, osteoinduction is achieved if the polarity of the field in the region is electronegative while bone in regions where the field is electropositive undergoes osteolysis.

Currently, some risk of non-unions may be reduced using implantable or external electrical stimulators. Many existing implantable stimulators use hermetically-sealed, constant-current DC power sources attached to one or more electrodes, which can be large, unwieldy and prone to infection or complications. In addition, the electrodes of these implantable systems are long and are liable to break. Since implantable systems are designed to be placed along the length of the spine covering multiple vertebrae, they often migrate and may cause injury.

External stimulators are marketed by Biomet, Orthofix International and DJO Global. External stimulation systems use an AC signal generator connected to electrodes placed on the skin or to an induction coil, which introduces electrical fields in the volume of the spine and the volume enveloping it through induction.

The above mentioned systems suffer product specific disadvantages such as the complicated implantation procedures for the implantable systems and stringent patient compliance requirements for the external stimulators. Additionally, the risk of heterotopic ossification is not addressed by any present system. Specifically, similarly to rhBMP-2, existing electrical stimulation systems are aimed at reducing non-union rates through nonspecific, unguided osteoinduction.

Thus, there is a need in the orthopedic medical device field to create a new and useful system and method for dynamically stimulating bone growth. This invention provides such a new and useful system and method.

BRIEF DESCRIPTION OF THE FIGURES

FIG. 25 shows osteoinductive regions within the fusion space during stimulation using one embodiment;

FIG. 26 shows how it may be possible to select which region within the fusion space undergoes osteoinduction and osteolysis during stimulation using one embodiment;

FIG. 28A-28C show how it may be possible to select which region within the fusion space undergoes osteoinduction and osteolysis during stimulation for different placements of the implantable component;

DESCRIPTION OF THE EMBODIMENTS

Figure 1:
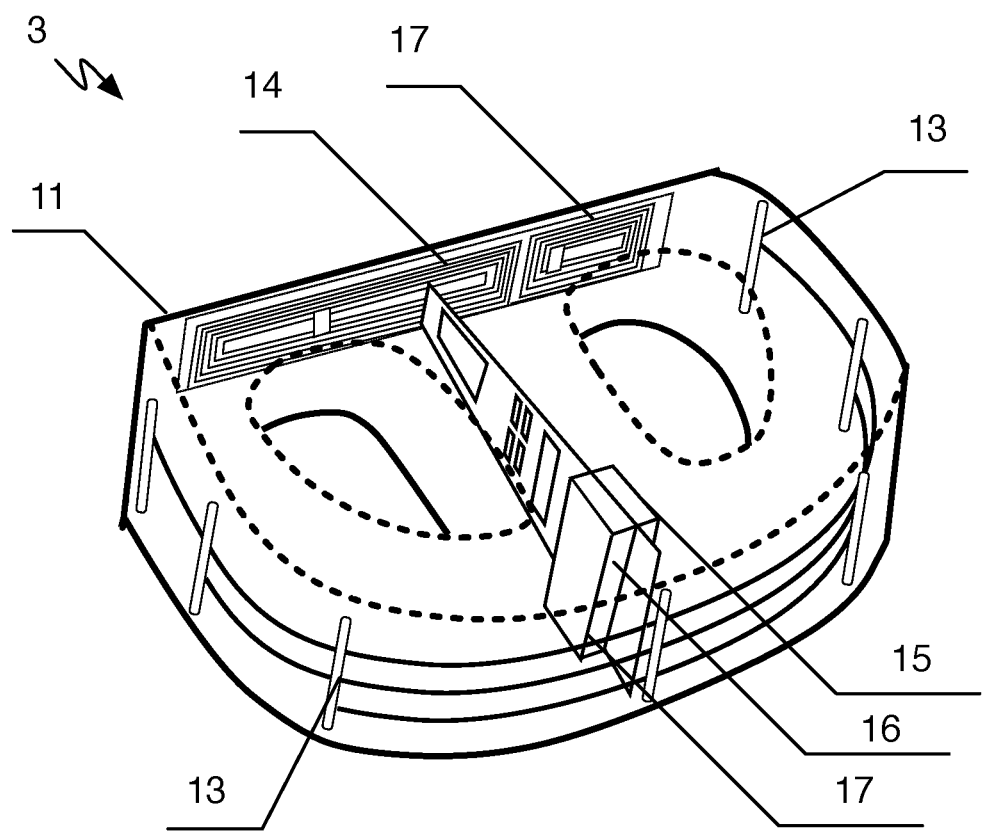
FIG. 1 is a perspective view of an implantable component of a preferred embodiment.

The following description of the embodiments of the invention is not intended to limit the invention to these embodiments but rather to enable a person skilled in the art to make and use this invention.

1. System and Method Overview

The system and method for dynamically stimulating bone growth of a preferred embodiment functions to provide an orthopedic implant with dynamic wireless electrical stimulation capabilities.

One optional objective of the system and method is to dynamically guide osteoinduction in the fusion space of an orthopedic implant to promote sufficient, but not excessive fusion mass in targeted regions. The system and method can preferably sculpt bone formation utilizing a plurality of independently, dynamically controllable electrodes which can be used synergistically to create non-overlapping volumes of osteoinduction and osteolysis. The process of determining targeted regions for osteoinductive or osteolytic stimulation may also benefit from a feedback mechanism monitoring the state of the fusion space. The system and method may optionally also include the capability to monitor bone growth in the fusion space electrically using impedance testing. Since impedance testing can be performed multiple times daily, its inclusion may facilitate rapid adjustments to stimulation settings aimed at addressing insufficient fusion mass production (risk of non-fusion) and/or heterotopic ossification. Such ease of monitoring has tremendous benefits over traditional approaches dependent on X-rays, CT scans, and the like.

In various implementations, the inventive implant system may comprise, in part, of a passive set of implantable component(s), which are implanted subcutaneously. The passive set of implantable component(s) is preferably characterized as passive by not having a battery or active an independent energy supply. In various embodiments, energy needed to set up potential gradients utilized to drive current between electrodes and to carry out all other functions carried out by the implantable component(s) may be provided wirelessly by one or more non-implantable component(s). Such non-implantable component(s) are not implanted and may include a power source such as a battery. Alternative, embodiments may have an active set of implantable component(s) which may include a battery, an energy harvesting system, or other suitable active energy source that may not be fully reliant on a non-implantable component as source of wirelessly transmitted power.

The implantable component(s) may also comprise of one or more medical implant bodies. The implant body or bodies are preferably non-conductive, but may be partially conductive. Such medical implant bodies may house some or all circuit elements, PCB, leads, antennas etc. included as part of the implantable component(s). In various implementations, these medical implant bodies may also include integrated electrode sites which may be distributed across the geometry of the implant bodies in such a way as to facilitate the generation of osteolytic or osteoinductive regions throughout the fusion space. An osteolytic region promotes osteolysis or the active reabsorption of bone matrix. An osteoinductive region promotes bone growth. The electrodes can be conductively isolated from a subset of the other electrodes and more preferably conductively isolated from each of the set of electrodes such that each electrode could be independently controlled. In some embodiments, the medical implant body comprises a spinal implant, which may be a spine cage. The spine cage may be made of a polymer, such as PEEK, or it may be made of engineered natural or synthetic bone material or some other material or any combinations thereof. In other embodiments, the implant body may take the form of a thin shape (e.g., a surface form factor), which can be placed, attached or non-attached, enveloping a spinal cage. In yet other embodiments, the implant body may take the form of a thin shape, which may be placed within any area within or in the vicinity of the intervertebral space.

As a first potential benefit, the system and method may provide dynamic and controllable stimulation while implanted within a patient. The system and method can be configured to selectively create regions of osteolysis and osteoinduction thereby simultaneously addressing both the risk of non-fusion and the risk of heterotopic ossification following spinal fusion surgery. To this end, the implant system may include a plurality of independently controllable electrodes, spatially distributed such that current driven between different subsets of electrodes can be used to generate osteolysis and osteoinduction within one or multiple target bone volumes. Utilizing an adequate number of electrodes (at least 3) distributed strategically throughout the fusion space, synergistic combinations of anodes and cathodes may be used to create regions of osteolysis and osteoinduction in multiple volumes of bone located at multiple locations within the fusion space. This method may be used to sculpt fusion mass quantity and distribution towards a shape that benefits fusion outcomes by steering both the magnitude and location of increased or decreased fusion mass. To further aid sculpting of the fusion mass, certain implementations of the inventive implant system may also include circuitry to adjust the intensity of delivered stimulation by adjusting the amplitude of current driven between electrodes. Such adjustments may increase or decrease the volume of bone affected by stimulation and/or increase or decrease the effect with which stimulation causes osteoinduction and/or osteolysis within volumes of bone affected by an applied stimulation.

As a second potential benefit, the system and method may provide seamless integration of electrical stimulation to static orthopedic implants. The system and method in one variation can be integrated into a form factor of existing implants offering a consistent experience to doctors familiar with use of the form factor of implantable devices currently on the market. In one variation, the system and method could include an implantable component offered in a form factor of an orthopedic implant such as a spinal fusion cage. In another variation, the system and method could include an implantable component configured to augment a secondary orthopedic implant by physically coupling with an orthopedic implant, which may offer enhanced versatility for a wider variety of implants. For example, the system and method may be applied to an implantable component that wraps around or physically couples with an existing implant device (e.g., a spinal cage) as shown in FIGS. 6A-6D. In another variation, the system and method may be applied to a distributed set of implantable components wherein multiple implantable components cooperatively provide stimulation. For example, two implantable components that have been surgically inserted in two distinct locations may generate a resulting field of electrical stimulation by cooperatively activating their respective electrodes as shown in FIG. 6D. Communication, power, and processing capabilities can be shared, coordinated, or independently operated within a distributed implantable variation.

As a third potential benefit, the system and method of some embodiments may enable a mechanism for monitoring bone growth within the fusion space. Bone growth monitoring can function to allow the inventive implant system to rapidly respond to changes in fusion mass distribution within the fusion space during the fusion process. Bone growth may be monitored by performing impedance measurements between pairs of single or multiple electrodes so that the impedance of the tissue between such pairs can be monitored. Since the impedance of bone is different than other tissue, a change in impedance between a pair may be used to estimate state of the fusion mass between that pair. An adequate number of electrodes (at least 3) distributed strategically throughout the fusion space may facilitate the monitoring of fusion mass throughout the fusion space. In various implementations, all or a subset of the plurality of electrodes that may be included as part of the implantable stimulation system may be used to both deliver stimulus and/or serve as electrode pairs between which impedance can be measured. In various embodiments, measured impedance data may be used to adjust the amplitude of stimulation, choice of stimulation electrodes, and/or the polarity of all stimulating electrodes based on preprogrammed embedded algorithms either automatically or following authorization by health care professionals. In various implementations, measured impedance data may be provided to patients and/or healthcare professionals providing a means of monitoring the fusion progress. In some implementations, healthcare professionals may also use the impedance data and/or other fusion monitoring mechanism to adjust the amplitude of stimulation, choice of stimulation electrodes, and/or the polarity of any stimulating electrodes.

As a fourth potential benefit, the system and method of some embodiments may enable non-implantable components to be housed within existing recovery supports and braces, which may reduce the reliance on patient compliance relative to implementations where a non-implantable components are stored in other housings. In some embodiments the non-implantable component(s) may be housed in a cervical collar or lumbar corset similar to those commonly worn by patients following spinal cord surgery—cervical collars and corsets are already worn by about half of all patients having undergone spinal fusion surgery. An implementation of the system or method using a non-implantable component integrated with a cervical collar or corset may reduce the reliance on patient compliance relative to implementations where the non-implantable component(s) are contained in other housings. Another benefit is that cervical collars and lumbar corsets worn by patients following spinal fusion surgery often have surfaces located in close proximity to the fusion space and typically rotate minimally around the longitudinal axis. In various embodiments, the transmitter coil(s), RF antenna(s), ultrasonic transducer(s), and/or other wireless power transmission elements may be contained within a volume just normal to one or more such surfaces to facilitate stable and high-energy transfer efficiency between the implantable or non-implantable component(s).

2. System for Dynamically Stimulating Bone Growth

As shown in FIG. 1 system for dynamically stimulating bone growth of a preferred embodiment can include an implantable component 3 with implant circuitry 12 integrated in an implant body 11, wherein the implant circuitry includes implant receiver circuitry 14, implant control circuitry 15, and a plurality of electrodes 13. The implantable component 3 can function as a surgically inserted orthopedic device that can dynamically deliver electrical stimulation and/or bone growth monitoring. The implantable component is preferably wireless, and accordingly the system can include at least one non-implantable component 2 that includes a power source 18, a transmitter circuitry 19, and optionally transmitter communication circuitry, which functions to wirelessly deliver power to and/or communicate with the implantable component 3.

Figure 2:
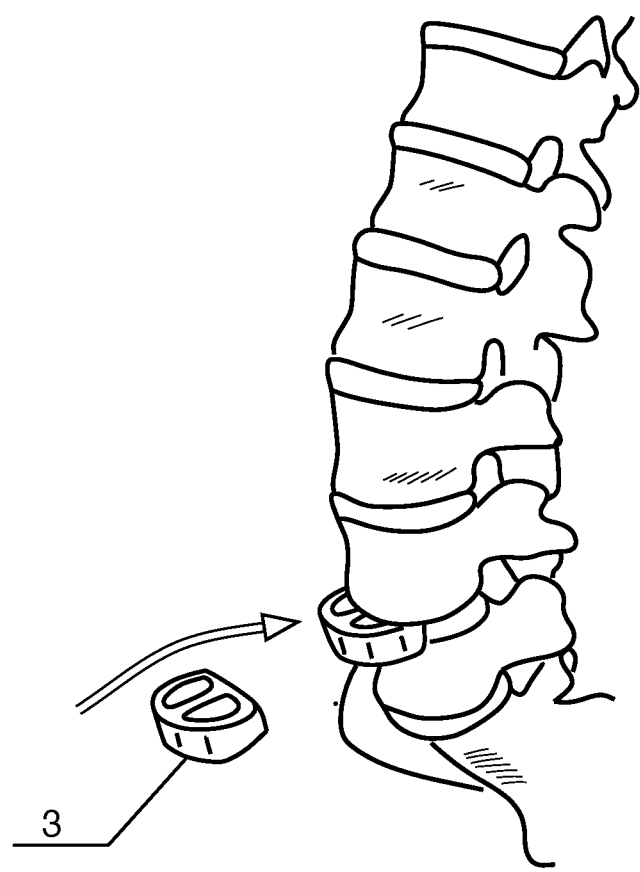
FIG. 2 is a schematic representation of an exemplary surgical use of an implantable component.

The system can be used in a wide variety of applications that use orthopedic implants such as in a spinal fusion operation. In a spinal fusion operation, the implantable component 3 is inserted into the spine as shown in FIG. 2. Additionally, external portions of the system (e.g., a non-implantable component 2) may be integrated with apparatuses common with the corresponding procedure. For example, cervical collars and lumbar corsets can include a wireless power transmitter for a spinal fusion implementation of the implantable component 3.

An implantable portion, such as a spine cage, that includes a receiver tuned to the transmitter, and a plurality of electrodes. The external transmitter includes a transmitter circuit that generates a signal that can be wirelessly transferred to the receiver. The implanted receiver includes a tuned receiver, a rectifier circuit, and a controlled current source. In addition it contains logic for setting the state of each electrode site (anode, cathode or passive) and optionally circuitry to perform impedance measurements. The implantable portion may be completely passive, and contain no batteries or other active power source. Instead, the implantable portion may be powered wirelessly by the transmitter.

The system may alternatively be applied to other medical spaces where an implant could provide electrical stimulation or bone growth monitoring (or other applications of impedance monitoring). Herein, the use case of a spinal fusion orthopedic implant is used as a primary example, but one knowledgeable in the art could appreciate how the system may be applied to other implant applications.

In other embodiments the non-implantable component(s) may be housed in a cervical collar or lumbar corset similar to those commonly worn by patients following spinal cord surgery and the implantable component(s) may, in part, comprise of a spinal cage. In some embodiments, the implantable stimulation system may be seamlessly integrated into standard spinal fusion surgery with the housing of the non-implantable component(s) serving the role of a cervical collar or lumbar corset and the implantable component(s) serving the role of a spinal cage.

In various embodiments, the implantable and non-implantable component(s) may include circuitry to store, process and wirelessly communicate data and control signals between the implantable and non-implantable component(s) and between non-implantable component(s) and user interface components. Examples of data that may be communicated between implantable and non-implantable component(s) and non-implantable component(s) and user interface components include control signals specifying the magnitude of stimulation, control signals specifying the state of electrodes during stimulation (anode, cathode, passive), control signals specifying the frequency, duty cycle and mode of stimulation (AC or DC etc.), control signals specifying the shape of the stimulus waveform, control signals specifying the scheduling or frequency of stimulation, control signals specifying the frequency of impedance measurements, diagnostic data communicating the state of the implantable component including any discrepancies between received and consumed electrical power, diagnostic data communicating the state of the non-implantable component including the state of the power source, and data communicating results from impedance measurements.

In various embodiments, systems and methods are disclosed for altering the electrical environment within and, optionally, measuring the impedance of target tissue such as bone. In various embodiments, one or more implantable component(s) may be utilized to drive current between a plurality of electrodes thereby generating volumes of electronegative or electropositive fields aimed at causing osteoinduction and/or osteolysis of bone tissue. In some implementations, one or more implantable component(s) may optionally be used to drive current between pairs of single or groups of electrodes with the goal of measuring the impedance of the tissue in-between the pairs. Herein, the system and method will primarily be described as using a single implantable component 3, though it may reasonably be extended to multiple implantable components 3.

Figure 3:
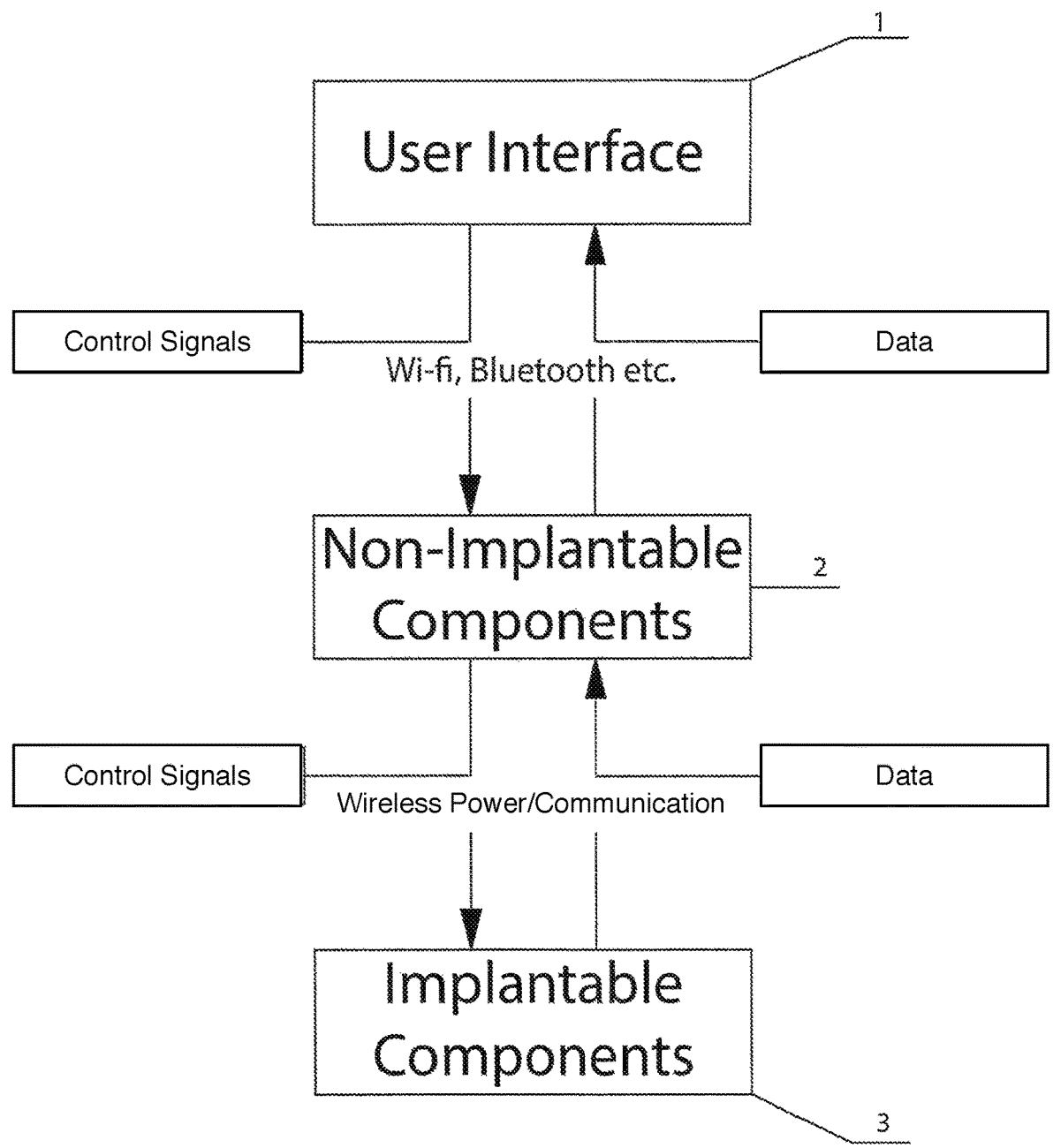
FIG. 3 is a system overview of a system of a preferred embodiment.

As shown in FIG. 3, an example embodiment of the system includes user interface components 1 which can enable a desired user to interact with the non-implantable 2 and/or implantable component(s)$_3$. In the shown example embodiment, control signals and/or data may be sent between the user interface components and the non-implantable component(s) wirelessly using wireless technology including, but not limited to Wi-Fi® or Bluetooth®. Almost all contemporary PC, tablets or smart phones includes Wi-Fi capability, and Wi-Fi capability may be included in the non-implantable component(s) using a Wi-Fi enabling microcontroller such as Texas Instruments CC3200. Furthermore, according to the example embodiment, control signals and power and/or data may be sent between the non-implantable and the implantable component(s) wirelessly using induction or other wireless transmission modes. A single or a plurality of wireless links (e.g., inductive links) operating at different frequencies could be used to send signals between the implantable 3 and the non-implantable component(s) 2. Alternatively, control signals, power and/or data may be sent between the non-implantable and implantable components using other modalities. The other wireless modalities preferably use electrical radiative coupling such as RF irradiation, but can additionally include ultrasound, infrared radiation (IR), and/or any suitable wireless communication/power transmission approach.

Figure 4:
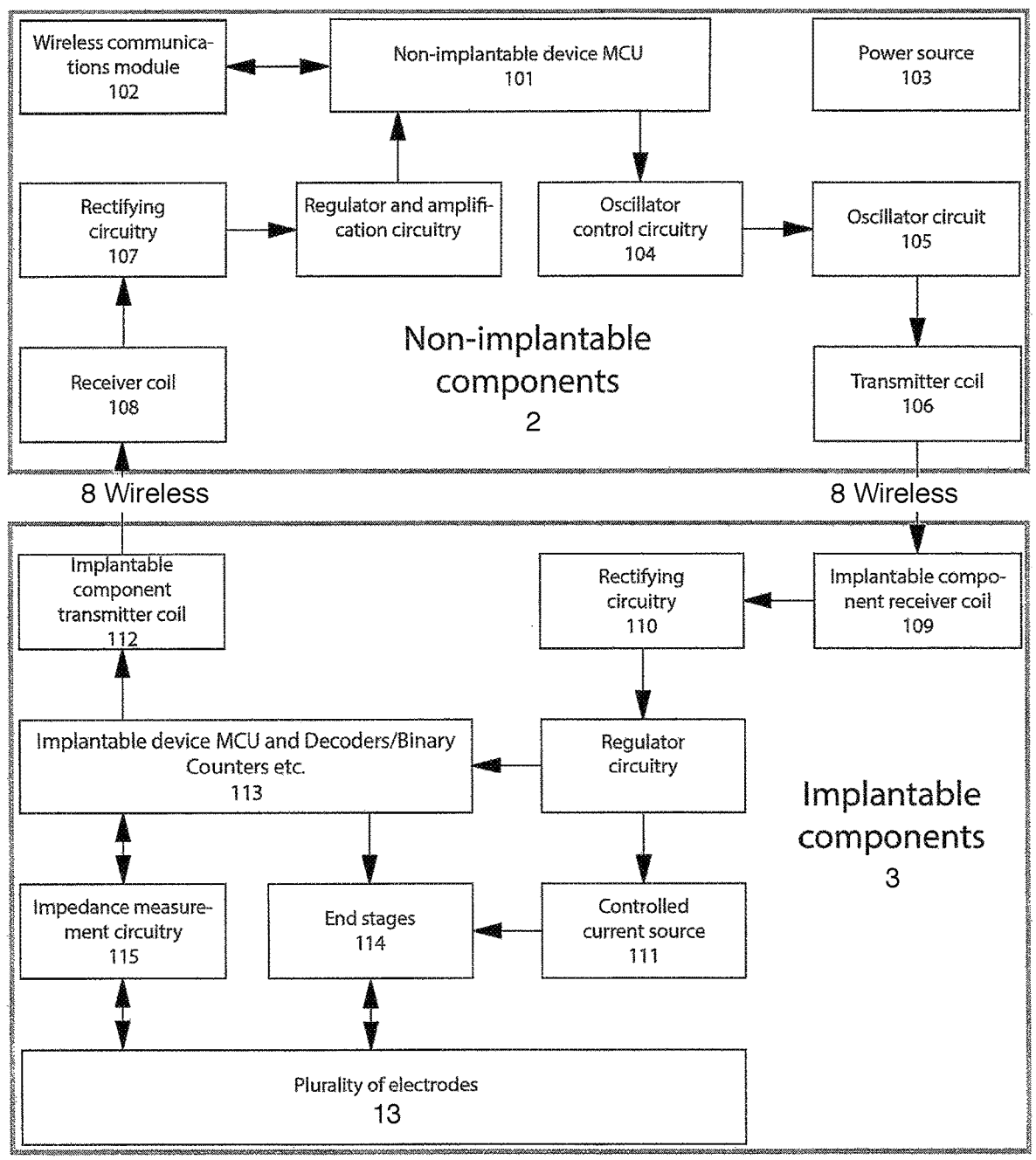
FIG. 4 is a detailed system overview of elements of a system of a preferred embodiment.

FIG. 4 shows a block diagram depicting the makeup of one example embodiment of the implantable 3 and non-implantable component(s) 2. In the illustrated embodiment, the non-implantable component(s) comprises of a power source 103; a wireless communications module 102; a controller such as microcontroller 101; a tuned receiver coil 108; oscillator control circuitry 104; an oscillator circuit 105; and a transmitter coil 106. The circuit implementation of the systems described herein can use any suitable approach. Where a discrete, component level description is used herein as one example implementation, one knowledgeable in the art would appreciate that such circuit design approach may be achieved through an application-specific integrated circuit (ASIC) and/or any suitable circuit design approach.

2.1 Implantable Component

The implantable component 3 of a preferred embodiment can function to provide controllable stimulation and/or monitoring of bone growth when implanted in a patient. The system can comprise a single implantable component 3. Alternatively, the system may include a set of implantable components 3. A set of implantable components may operate cooperatively such as by delivering stimulation to the body across at least two implantable components 3 or by monitoring bone growth between at least two implantable components 3.

In various embodiments, implantable component(s) 3 may include circuitry to receive/send signals and receive power from non-implantable component(s) 2. A set of implantable components may share wireless power and/or communication delivery from one or more shared non-implantable components 2 but may alternatively each be connected to or coupled to an individual non-implantable component 2. Implantable component(s) 3 may also include circuitry that can be used to control which regions of the fusion space receives osteoinductive or osteolytic stimulation and the magnitude of such stimulation. In some embodiments, the implantable component(s) 3 may also include circuitry to measure the impedance of tissue within the fusion space. In various embodiments, the implantable component(s) 3 may include circuitry to store/process impedance measurement data and/or sending said data to the non-implantable components.

More specifically, the implantable component(s) 3 may individually or collectively include an implant body 11; implant circuitry 12; and a plurality of electrodes 13. The implant circuitry 12 can include implant receiver circuitry 14 for wireless power transfer from a non-implantable component 2, control circuitry for controlling delivery of electrical stimulation from the electrodes, and/or bone growth monitoring circuitry 16 for measuring bone growth metrics. Additionally the implantable component 3 can include implant communication circuitry 17 to communicate with other components of the system.

In various preferred implementations, the implantable component(s) may be passive and the electric energy required to set up the potential gradients resulting in net current flow between electrodes can be supplied wirelessly from one or more non-implantable component(s). Herein, passive describes the design of the implantable component 3 without an active power supply such as an onboard battery. Alternative embodiments may include an active battery or other active power source, which can be used in place of the wireless power approach or used as a supplemental power source.

The power delivered wirelessly to the implant may be utilized to produce an electrical field within the patient by driving current between electrodes (including one or more of cathodes and at least one anode) located across the surface of the implant. In addition to directionality, the frequency, and amplitude of the electrical stimulation provided by the device can also be adjusted.

The implantable component 3 may be incorporated into a cage made of a non-conductive material. The implant may be powered wirelessly by a non-implantable component 2 with a transmitter incorporated in a cervical collar, corset, and/or another suitable object worn by the patient or positioned near the patient following conventional spinal surgery.

The implant body 11 of a preferred embodiment functions as the structural element housing or holding the subcomponents of the implantable device 3 such as the implant circuitry 12. The implant body 11 is preferably made of non-conductive material, but may be partially conductive. Such medical implant bodies may house some or all circuit elements, PCB, leads, antennas etc. included as part of the implantable component 12. In various implementations, the implant body 11 may also include integrated electrode sites which may be distributed across the geometry of the implant body 11 in such a way as to facilitate the generation of osteolytic or osteoinductive regions throughout the fusion space. When the implant body 11 is non-conductive, current is only applied at the surface of the electrode sites, thus allowing the distribution of current density to be controlled by the placement of the electrodes as well as their state during stimulation. Alternatively, the electrodes can be conductively isolated from a subset of the other electrodes and more preferably conductively isolated from each of the set of electrodes such that each electrode could be independently controlled such that current density may be similarly controlled. In some embodiments, the implant body 11 can be a spinal implant, which may be a spine cage. The spine cage may be made of a polymer, such as PEEK, or it may be made of engineered natural or synthetic bone material or some other material.

FIG. 1 is a perspective view of the implantable portion of the medical implant system according to one embodiment wherein the implantable component(s) comprises, at least in part, by a spine cage. The illustrated implantable spine cage 10 comprises a non-conductive medical implant body 11, implant circuitry 12, and a plurality of electrodes 13.

Figure 5:
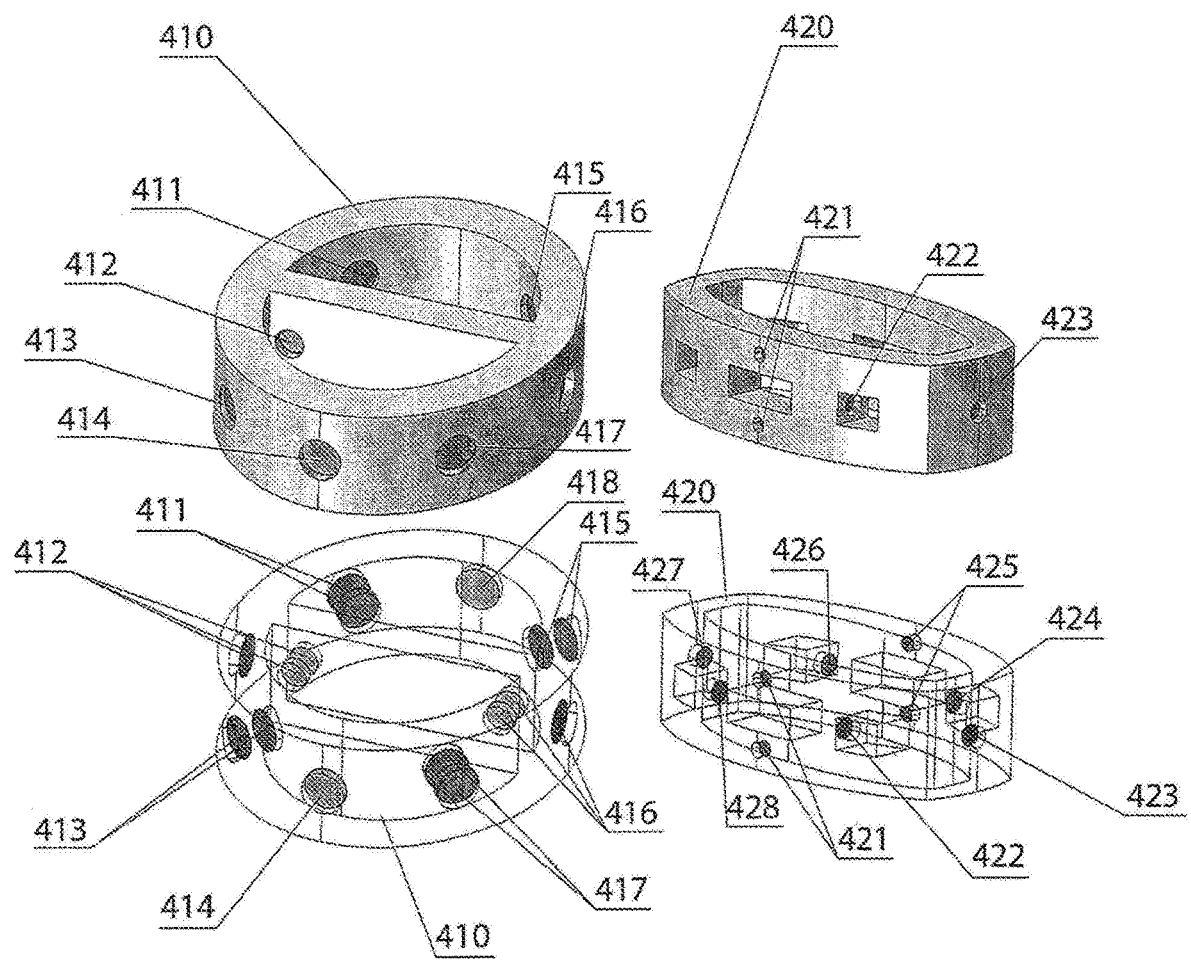
FIG. 5 is a perspective view of two spinal cage variations of implantable components.

The implantable component 3 can be incorporated into a variety of geometries of spinal cages including but not limited to anterior lumbar interbody fusion (ALIF) cages, transforaminal lumbar interbody fusion (TLIF) cages, eXtreme lateral interbody fusion (XLIF) cages, posterior lumbar interbody fusion (PLIF) cages, anterior cervical fusion (ACF) cages, and/or other suitable types of spinal cages. In some implementations the spinal cage geometry is an extruded prism of some defined form, which generally has a continuous outline. The spinal cage can include one or more graft windows, which can be defined as internal cavities. The spinal cage may include other design features such as surface coatings, surgery tool attachment points, teeth, and/or other elements. The spinal cage is preferably composed of a non-conductive polymer such as PEEK but may be made of engineered, natural, or synthetic bone material, titanium and/or other suitable material(s) or combinations thereof. The implantable component 3 can alternatively be incorporated into a variety of other medical implants. The implantable component 3 can be customized for a variety of spinal cage geometries and designs (as shown by the two commonly used spine cage geometries (410 and 420) represented in FIG. 5. A first implementation 410 contains 16 electrode sites connected to 8 end stages (411-418). A second implementation 420 contains 10 electrode sites connected to 8 end stages (411-428). The implantable component 3 may alternatively be integrated into any suitable type of medical implant used for alternative orthopedic procedures.

As described above, the implantable component 3 may be configured to augment a secondary orthopedic implant by physically coupling with an orthopedic implant. The orthopedic implant may be any suitable type of an implant such as a non-stimulation ALIF, TLIF, XLIF, PLIF, or ACF spinal cage. The implant augmentation variation may use a variety of approaches.

Figure 6A:
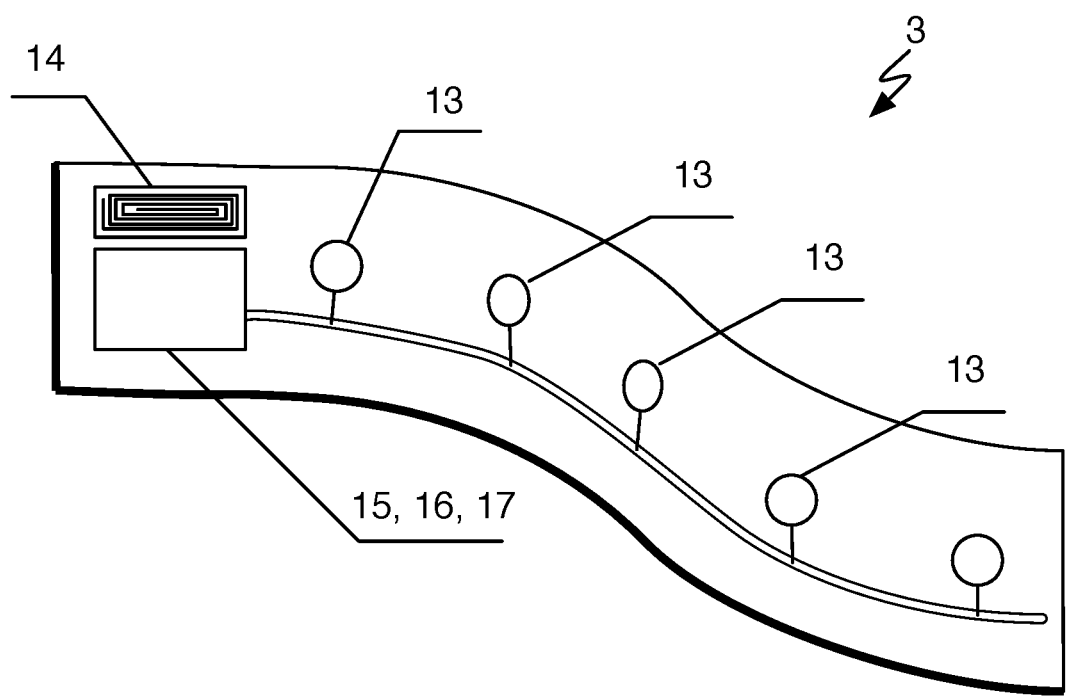
FIGS. 6A-D are schematic representation of alternative form factors of an implantable component that may be used with an existing implant.

In a first variation of an implant augmentation design, the implantable component 3 may be produced in a thin surface "film" form factor as shown in FIG. 6A, which can be placed, attached or non-attached, enveloping a spinal cage. The film implantable component is preferably flexible. A film implantable component 3 in one variation could wrap around a medical implant structure and adhere or be fixture to the implant structure. A film implantable component 3 in a second variation may be a thin sleeve that slips over or around an implant structure.

Figure 6B:
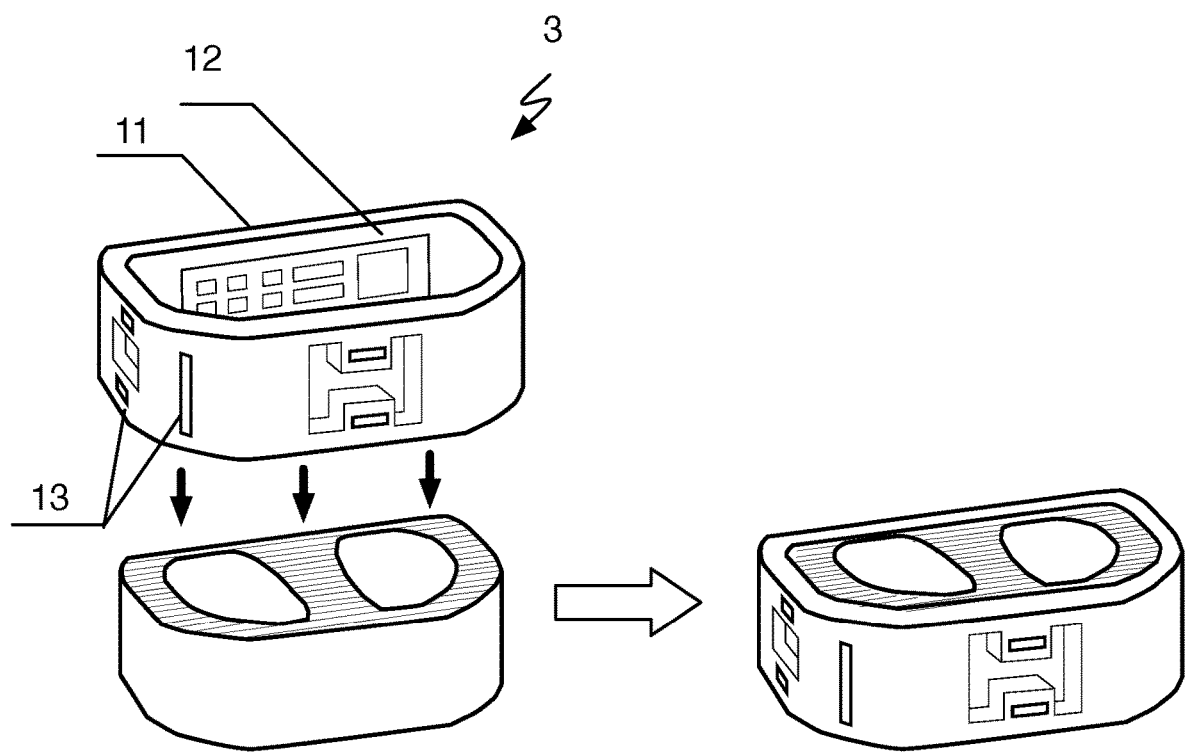
Figure 6C:
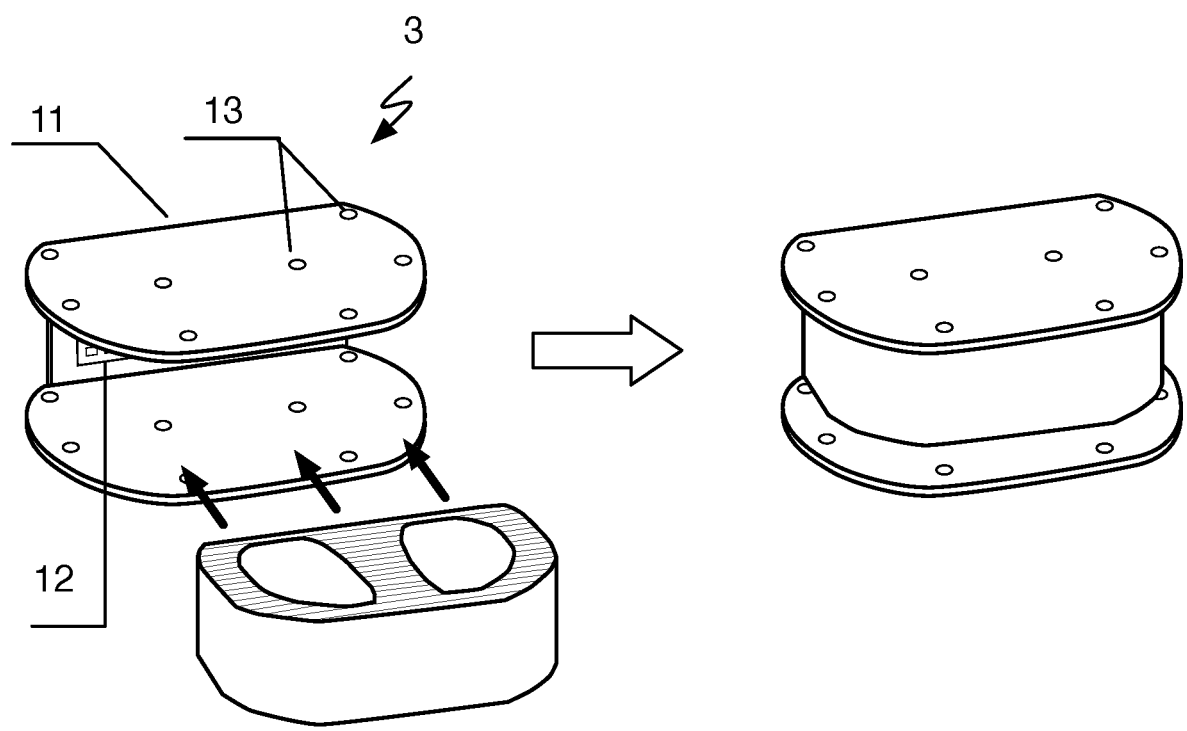
Figure 6D:
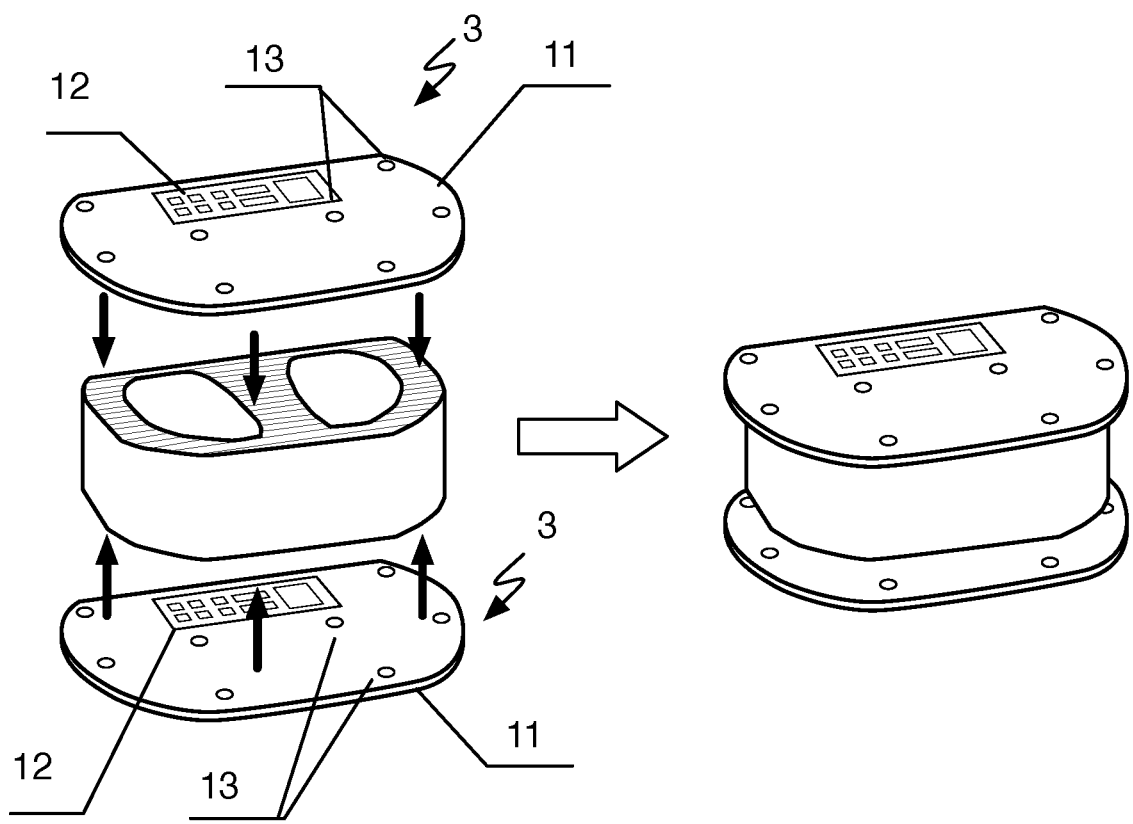

In another variation, the implantable component 3 can be a surrounding ring that is fixture around the outside of an implant as shown in FIG. 6B. In a similar variation, the implantable component 3 can be a clip that an implant fits within as shown in FIG. 6C. In yet another variation, the implantable component 3 may be an insert, which may be fixed to some portion of the implant structure such as within the internal cavity of a spinal cage. In yet other embodiments, the non-conductive implant body may take the form of a thin shape, which may be placed within any area within or in the vicinity of the body such as an intervertebral space. For example, the implantable component 3 may be surgically positioned or fixed in the body, wherein the structure dynamics do not provide a substantial medical function. In another variation, the implantable component can be a distributed set of implantable components 3, wherein at least a subset of the set of implantable components 3 physically couple with an implant. As shown in FIG. 6D, two plate-based implantable components can be fixtured to two opposing surfaces of an implant.

As one potential benefit of the adhesive film embodiment, customized configurations could be generated for a wide variety of orthopedic implants. Similarly even for a single type of orthopedic implant, a set of different electrode configurations could be made to target particular stimulation objectives. Computational design approaches can be used to design customized electrode placement and configuration and then surface fabrication approaches can be used to produce a customized implementation of an implant component 3.

The implant circuitry 12 of a preferred embodiment functions to enable electronic stimulation and/or bone growth monitoring. The implant circuitry 12 can be integrated in one site of the implant body 11, but may alternatively be integrated at multiple locations within the implant body 11. The implant circuitry 12 can be composed of various processing units (e.g., microprocessors), circuit elements, conductive leads, antennas, and other various electric components. As described above the implant circuitry 12 can include: implant receiver circuitry 14 effective for converting energy emitted by the transmitter to an electrical current; implant control circuitry 15 effective to control one or more of said electrodes with respect to whether electric current is flowing through the electrode or is not flowing through the electrode, and, when current is flowing through the electrode, with respect to one or more characteristics of the current flowing through the electrode; bone growth monitoring circuitry 16 effective to measure impedance of the tissue between electrodes as a signal of bone growth in that region; and/or implant communication circuitry 17 effective to communicate with a non-implantable component.

A preferred implementation of an implantable component 3 includes at least the above circuitry components such that power can be delivered wirelessly, stimulation can be controlled, bone growth can be monitored, and communication can be established between the implant component 3 and a non-implantable component 2. Alternative embodiments may do without wireless power, controllable stimulation, bone growth monitoring, or communication. For example, an implantable component with an alternative power source may not need the components for wireless power. Similarly, a variation of implantable component 3 may be designed for stimulation without bone growth monitoring or alternatively be designed for bone growth monitoring without stimulation. The implant circuitry 12 can include any additional circuitry components such as additional sensors or stimulating elements. In one variation, the implant circuitry 12 may include at least one grounding electrode lead that establishes a reference voltage (e.g., ground).

The implant receiver circuitry 14 of a preferred embodiment functions to wirelessly couple with an external power source. The implant receiver circuitry can be effective to convert an external wireless power transmission to an electrical current. A wireless power signal is preferably generated outside and couples with or can be harvested by the implant receiver circuitry 14. Preferably, the implant receiver circuitry 14 is effective to convert an electromagnetic field to an electrical current. The wireless power transmission can alternatively be an acoustic, or other suitable form of power transfer medium. The implant receiver circuitry 14 receives energy generated by a transmitter wirelessly, and uses that energy to set up potential gradients utilized to drive current between electrodes and to carry out all other electrical functions carried out by the implantable component(s). The implant receiver circuitry 14 is preferably effective for converting said electromagnetic field to an electrical current (e.g., an oscillating current), and in some implementations the implant receiver circuitry 14 may produce a current of between about 10 µA and 200 µA. The implant receiver circuitry 14 system preferably includes a receiver element and a power management system. Power is preferably transferred through electric radiative or inductive coupling between tuned antennas. Alternative forms of wireless power transfer may alternatively be used. The power management system can be used to adjust the power which may include converting from AC to DC, regulating, or augmenting the received power prior to being used by at least one component of the implant circuitry. Additionally, the implant receiver could include a temporary power storage solution to provide a steady current source with brief interruptions or changes in wireless power transfer. For example, a capacitor could be used as a temporary power source.

The implant control circuitry 15 of a preferred embodiment functions to control the current provided to the electrodes. In some embodiments the implant control circuitry 15 may be effective to control one or more of said electrodes with respect to the polarity (current source or current sink) and/or state (current source/sink, or passive) of the electrode during stimulation. Similarly, the implant control circuitry 15 may be effective to control one or more of said electrodes with respect to the current amplitude flowing through the electrode. The implant control circuitry 15 is preferably effective to control one or more of said electrodes independently of any control provided to other electrodes. In another variation, a subset of the electrodes may be conductively coupled and be controlled simultaneously. In some instances, all of the electrodes may be driven, but in other conditions, only a subset of the electrodes may be used for stimulation. The implant control circuitry 15 can drive the electrodes at least in part based on the state of the implant receiver circuitry 14. When and how the electrodes are driven can depend on the available power. During stimulation the implant control circuitry 15 could be driven to establish a steady state potential difference between at least two electrodes. Alternatively, the stimulation driven by the implant control circuitry 15 may be a signal such as a pulsing signal. The implant control circuitry 15 can be conductively coupled to each of the electrodes. Alternatively, a set of output selectors (e.g., demultiplexers) could be used to selectively drive electrodes. In this variation, the implant control circuitry 15 could be used to cycle through different electrodes.

In an alternative implementation, the electrodes are directly driven based on implant receiver circuitry 14 without active management of stimulation. In this variation, a non-implantable component 2 can control the stimulation by regulating the power signal transferred through the receiver circuitry 14.

The plurality of electrodes 13 of a preferred embodiment function as sites driven to various electric potentials to induce electric current into the regions around the implantable component 3. An electrode is preferably a conductive element that includes an electrode site (e.g., a conductive pad exposed to body tissue) connected (directly or indirectly) to the implant control circuitry 15 through a conductive lead. The plurality of electrodes are preferably conductively isolated from the implant body and exposed at the set of distinct electrode sites on a surface implant body. The implant sites are preferably exposed on an outer surface of the implant body, which promotes conductively coupling with the surrounding body tissue. The electrode sites are distributed across the geometry of the implant bodies in such a way as to facilitate the generation of osteolytic or osteoinductive regions during a controlled stimulation mode. The electrode site geometry can be configured for differing current density profiles. The electrode sites can be uniform across the plurality of electrodes 13. Alternatively, there can be at least two different electrode sites with differing geometry. The surface shape of the electrode sites can be a circular conductive disk, a conductive strip, and/or any suitable shape. The electrode sites are preferably flush with the surface of the implant body. Alternatively, the electrode sites may protrude from the implant body or be recessed within the implant body. The conductive lead is preferably integrated within the implant body and is conductively isolated from other components. The plurality of electrodes 13 may be provided as an array of at least three electrodes, with the implant control circuitry 15 being effective to control the current flowing through the array of electrodes.

An electrode can be controlled to act as a source (e.g., cathode) or sink (e.g., anode) during electrical stimulation or to be passive in order to steer the current density in different parts of the intervertebral space. In some variations, a subset of electrodes may only be controllable between one or two states. For example, one electrode may only act as an anode and another electrode may only be driven as a cathode or be passive. However, the implant circuitry 12 preferably has full polarity control over each electrode.

Figure 29:
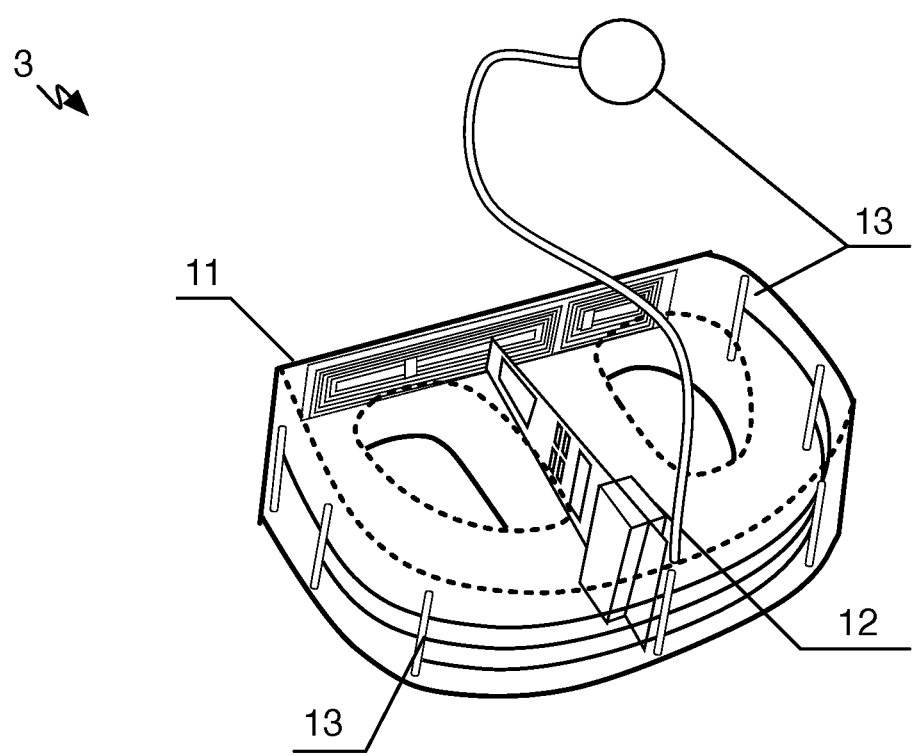
FIG. 29 is a schematic representation of an implantable component with a displaced electrode.

Additionally one or more electrodes may operate in a fixed polarity state. As mentioned above, the implant circuitry 12 may include at least one dedicated anode or grounding electrode lead that establishes a reference voltage (e.g., ground). A dedicated anode in one variation can be a fixed electrode with a larger surface (compared to at least one other electrode). The dedicated anode can be positioned in the rear region of the implant where bone growth is not desired. In another variation, the dedicated anode can be a displaced electrode as shown in FIG. 29. A displaced electrode can be an electrode that can be positioned away from the main body of the implant. A displaced electrode can include an electrical connector, which is preferably flexible but may alternatively be rigid. A displaced electrode may additionally be used as a cathode or as a dynamic electrode operating in different polarity states. In one example, a displaced electrode can be surgically positioned to provide a desired state of electrical grounding and/or promote a particular stimulation field. In one variation the plurality of electrodes 13 can include a fixed dedicated anode and a displaced dedicated anode.

In addition to producing electrical stimulations, the array of electrodes 13 may also be used to monitor the bone growth within the fusion space. Accordingly, the plurality of electrodes 13 may additionally be conductively connected to the implant bone growth monitoring circuitry 16. Monitoring bone growth involves driving AC signals between pairs of electrode site(s) and thereby measuring the impedance of the tissue located between the pairs. By doing this measurement between electrode pairs located on the outside perimeter of the implant it will be possible to generate an impedance profile of the entire fusion space. In the application of spinal fusion, the impedance profile can be used to monitor the degree of spinal fusion achieved and the data can be sent to the physician to assess if further intervention is necessary. The impedance profile can also be used alter the electrical stimulation—changing the polarity, changing the magnitude, changing the signal, or making any suitable stimulation change. This could be done automatically or after physician approval.

Figure 7:
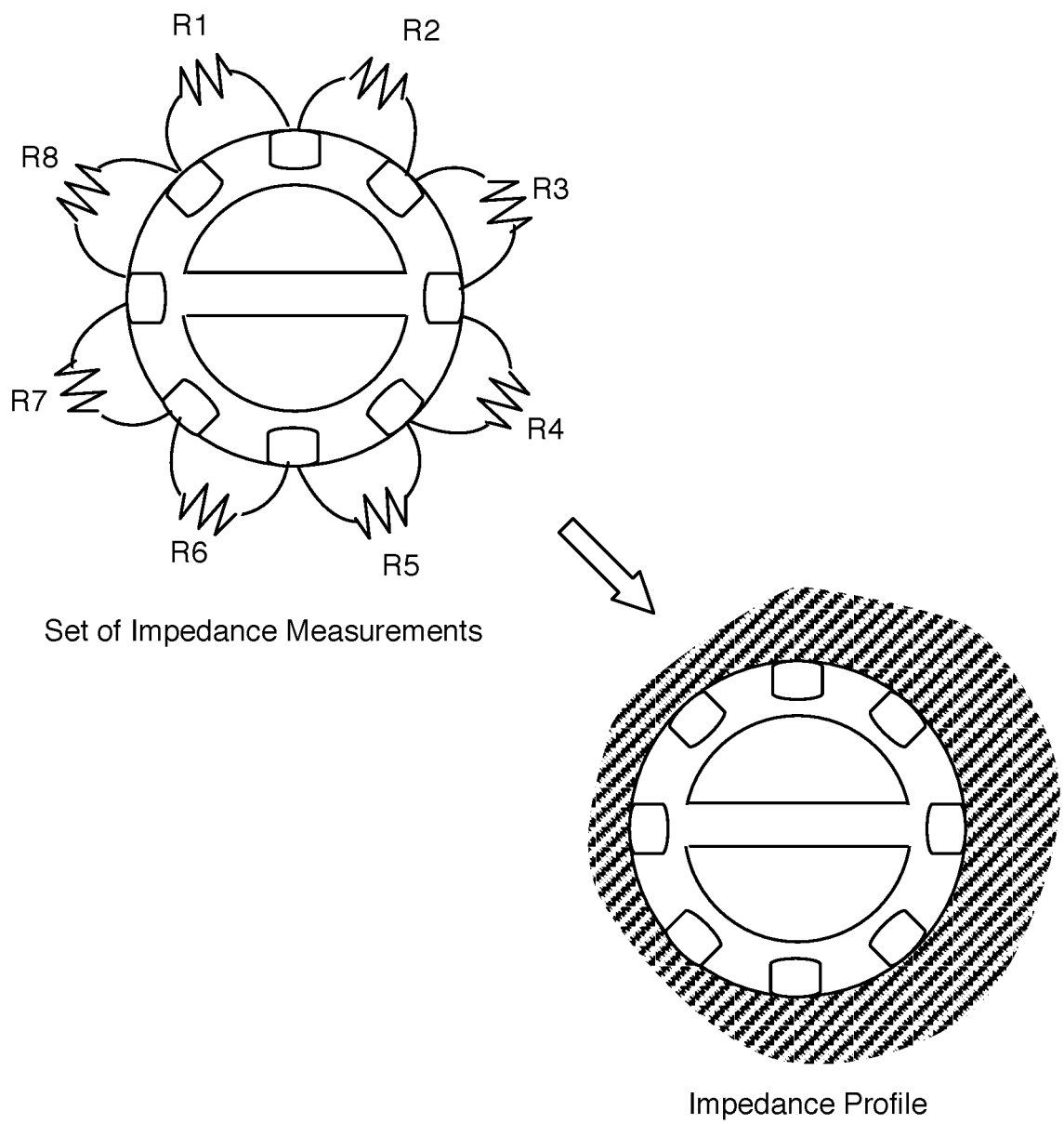
FIG. 7 is schematic representation of generation of an impedance profile from impedance measurements.

The implant circuitry 12 may include implant bone growth monitoring circuitry 16 which functions to measure bone growth from the implant component 3. Bone monitoring from the implant component 3 can be beneficial in reducing dependence on more complicated, slow, and expensive monitoring techniques such as ultrasound or x-rays conducted at a healthcare facility. The optional implant bone growth monitoring circuitry 16 can be used to measure the impedance of the tissue between pairs of one or more electrodes. The individual impedance measurements may be compiled into an impedance profile as shown in FIG. 7.

The measured impedance or bone growth data can be communicated to a non-implantable component 2. Additionally or alternatively, the data may be used internally in controlling the electrical stimulation delivered by the implant control circuitry 15. The impedance profile can be used to turn channels off or on, to change polarities, change stimulation magnitude, to change a stimulation signal, or make any suitable change to stimulation.

In one implementation, the plurality of electrodes 13 is connected to the bone growth monitoring circuitry 16 through a set of multiplexers such that impedance could be selectively measured between two electrodes. During an impedance check, the implant circuitry 12 can be configured to cycle through a set of impedance checks so that impedance can be measured in different regions around the implantable component 3. Preferably, impedance can be measured in substantially all the surrounding area of the implantable component 3. However, some variations may only be configured for measuring impedance in particular regions.

Figure 30A:
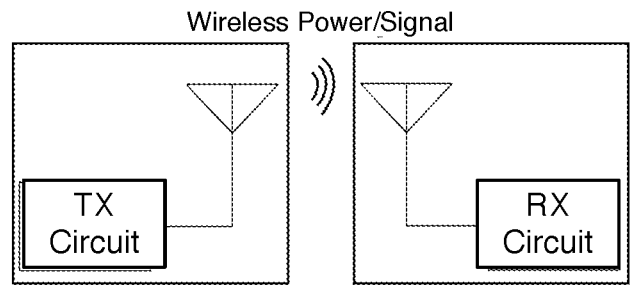
FIGS. 30A-C are block circuit diagrams of various power and communication transmission configurations.
Figure 30B:
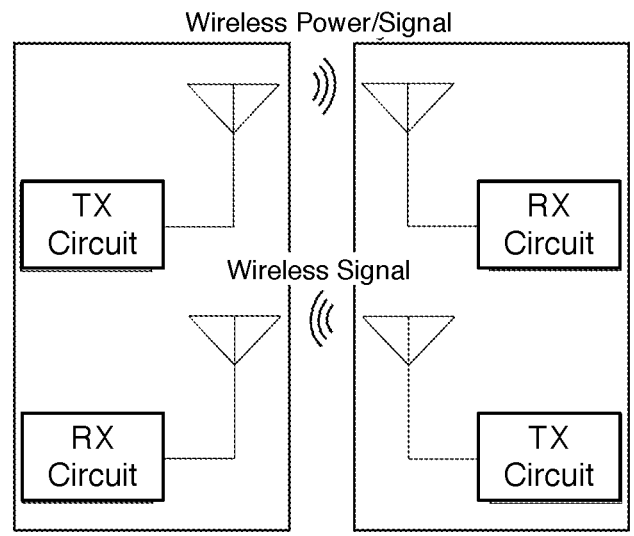
Figure 30C:
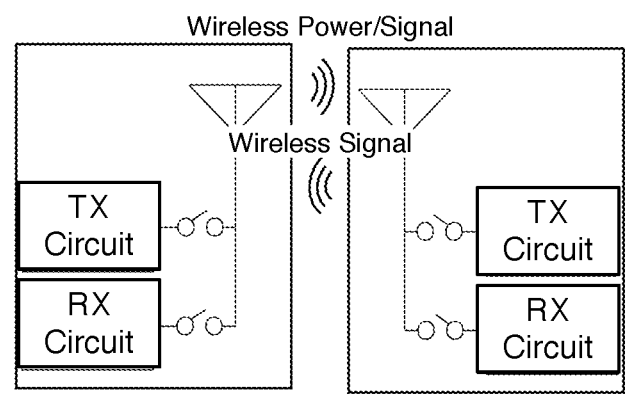

The implant circuitry 12 can additionally include implant communication circuitry 17, which functions to facilitate wireless communications with the non-implantable component(s) 2. One or more portions of the transmitter control circuitry may be wireless. Alternative implementations may use a wired or direct communication. The non-implantable component 2 can preferably communicate data to the implant component 3 as shown in FIG. 30A. In one implementation, data can be communicated through the wirelessly transmitted power signal. For example, a high frequency data signal could be transmitted on top of a lower frequency power signal. The data signal could be decoded or read during conditioning of the received power signal. Data from the non-implantable component 2 may include various commands relating to operational state directives, stimulation settings, bone monitoring settings, diagnostics settings, communication settings, and/or other suitable commands. The implant circuitry 12 can be used in sending data back to the non-implantable component 2. In one variation the non-implantable component may transfer power and data to the implantable component using a first dedicated set of tuned antennas and the implantable component may transfer data to the implantable component through a second, distinct set of tuned antennas as shown in FIG. 30B. In another variation, the non-implantable component may transfer data and power using a set of tuned antennas and the implantable component transfer data to the non-implantable component through the same set of tuned antennas as shown in FIG. 30C. Data from the implantable component 3 is preferably implant operating data that may include current settings, diagnostics results, bone monitoring data, stimulation logs, power status, and/or other information. Data from the implantable component may be held in local memory until successful transfer to a non-implantable component 2. In one variation, the power transmission can be modulated according to the power received by the implantable component 3. For example, if the power supply is not enough, the non-implantable component 2 may be instructed to adjust transmission (e.g., increasing transmission magnitude). In another variation, the bone growth data is communicated to the non-implantable component wherein a doctor or processing unit may determine if any changes should be made to the electrical stimulation.

In one particular implementation shown in FIG. 4, the implantable component(s) 3 comprises of a tuned air core planar receiver coil 109; rectifying circuitry 110; controlled current source 111; implantable component transmitter coil 112; implantable device microcontroller and decoders/binary counters etc. 113; end stages 114; a plurality of electrodes 13; and impedance testing circuitry 115. In the depicted embodiment, a receiver coil 109 part of the implantable component(s) 3 and a transmitter coil 106 part of the non-implantable component(s) 2 forms an inductive link where oscillating electric current within a transmitter coil 106 induces a potential over a tuned receiver coil 109 through inductive coupling. Alternatively, depending on the transmitter type, the implantable component(s) may include receivers suitable for receiving RF irradiation, waves generated by an ultrasonic transducer and/or IR (not shown). In the shown embodiment, AC current in the receiver coil can be converted into DC current using rectifying circuitry 110. The current source may additionally be amplified or regulated in any suitable manner. In one embodiment, capacitor(s) within the rectifying circuitry 110 may store energy received through a wireless link 8 and use it to meet the power consumption of the implantable component(s) 3. In one embodiment, the rectifying circuit 110 may also function as an envelope detector and the envelope of AC signals transmitted through a wireless link may be used to control the state of one or more implantable component(s) 3 either directly or indirectly through a microcontroller 113. In the depicted embodiment, a controlled current source 111 may be used to control the amplitude of current passed through a plurality of electrodes 116. In one preferred embodiment, the current source can control the amplitude of current passed through a plurality of electrodes 116 based on direct or indirect inputs from a microcontroller 113. In one preferred embodiment, the amplitude of the current passed through a plurality of electrodes 116 can be adjusted based on the fusion progress by changing the direct or indirect control input (e.g., from microcontroller 113) either using an embedded algorithm or based on inputs provided to microcontroller 113 from the non-implantable component(s) 2 through an wireless link 9. In the depicted embodiment, a microcontroller 113 may read in data from a wireless link; may directly or indirectly provide control signals to a controllable current source 111; may directly or indirectly provide control signals to end stage(s) 114, determining the state of one or more electrode(s) (anode, cathode, non-conductive/passive) within a plurality of electrodes 116 during stimulation; may directly or indirectly provide control signals to an impedance measurement circuitry 115, determining which pair of electrodes within a plurality of electrodes 116 impedance measurement may be conducted over; may directly or indirectly provide an AC signal to a impedance measurement circuitry 115 and may read back an output signal from an impedance measurement circuitry 115; may store and/or process impedance measurement data and may send impedance measurement data to the non-implantable component through an wireless link 9 by exerting direct or indirect control over the current passed through an transmitter coil 112. In some embodiments, a microcontroller 113 may adjust the states of the various components that it may exert control over directly. In another embodiment, a microcontroller 113 may adjust the state(s) of any components it may exert control over directly or indirectly by adjusting the state of any number and combination of optional circuit elements such as binary counters, decoders, oscillators, and/or summing gates etc. In the depicted embodiment, end stage(s) 114 can be used to adjust the state of one or more electrode(s) (anode, cathode, and non-conductive/passive) within a plurality of electrodes 116 during stimulation based on direct or indirect control input such as from microcontroller 113. In the depicted embodiment, an impedance measurement system may be used to measure the impedance between any two electrodes among a plurality of electrodes 116.

The implantable component 3 can have a variety of modes of operation. The implant circuitry could be configured to operate according to a complex state machine enable intelligent modifications and updates to the mode of operation. For example, various timing conditions, data thresholds, power thresholds, and/or other conditions could be used in automatically determining operating state. The implantable component 3 may alternatively use simple scheduling or basic operating logic in transitioning between states. In one implementation, operational state changes in the implantable component 3 are initiated through directives communicated from the non-implantable component 2. The implantable component 3 can include a diagnostics mode, a stimulation mode, an impedance monitoring mode, and a diagnostics mode.

A diagnostics mode functions to check the operational condition of the implantable component 3. The diagnostics mode can be performed prior to use in a surgery and/or after surgical insertion. The diagnostics mode may cycle through a variety of different system checks, which may include a power check, an electrode check, and a communication check. The power check verifies that sufficient power is delivered to the implantable component 3. The electrode check verifies the conductive state of each electrode. The electrode check can be performed in a manner substantially similar to the impedance measurements of the bone growth monitoring. The communication check can be a communication handshake between the implantable component 3 and the non-implantable component to verify data is being communicated properly. The power check may be performed periodically on a regular basis to ensure that sufficient power is transferred to the device. The electrode check may be performed less frequently such as every hour or every data since electrodes will likely not fail regularly. The communication check may be performed during any suitable communication handshake or at any suitable time.

A stimulation mode functions to electrically stimulate the body tissue in the vicinity of the implantable component 3. During a stimulation mode, the implant control circuitry controls the plurality of electrodes with respect to whether electric current is flowing through the electrode, and, when current is flowing through the electrode, with respect to one or more characteristics of the current flowing through the electrode. A stimulation configuration profile can define the desired characteristics of stimulation for a set of electrodes (e.g., specifying which electrodes are active, the polarity, and magnitude). As discussed above, the electrodes may be driven independently or together. Within the plurality of electrodes, at least a subset of the electrodes are set to a first potential and a second subset of the electrodes are set to a second potential such that current is induced between the first and second subset of electrodes. The electrodes are preferably driven so as to properly promote or deter bone growth (i.e., creating osteoinductive or osteolytic regions) throughout the fusion space. Stimulation could be stead state. Stimulation could also cycle through various charge profiles such as first promoting a charge across a first set of electrodes and then promoting a charge across a different set of electrodes. The polarities and magnitudes for different electrodes may additionally be updated over time.

Impedance monitoring mode functions to measure bone growth in tissue regions between electrodes. The impedance monitoring mode (i.e., a "bone growth monitoring" mode) can detect impedance of the surrounding tissue can be used in approximating bone growth. The implant control circuitry is configured to measure the impedance between a set of electrodes and generate an impedance profile when in an impedance monitoring mode. Impedance monitoring may additionally or alternatively be used in verifying operation of one or more electrodes. In yet another variation, impedance monitoring can be used in orienting the device after surgical insertion. The existing bone structure can be used as a reference for determining the position of the implant relative to a bone formation. Impedance monitoring is preferably performed at a different time as the stimulation mode but may alternatively be performed during stimulation mode.

Figure 8:
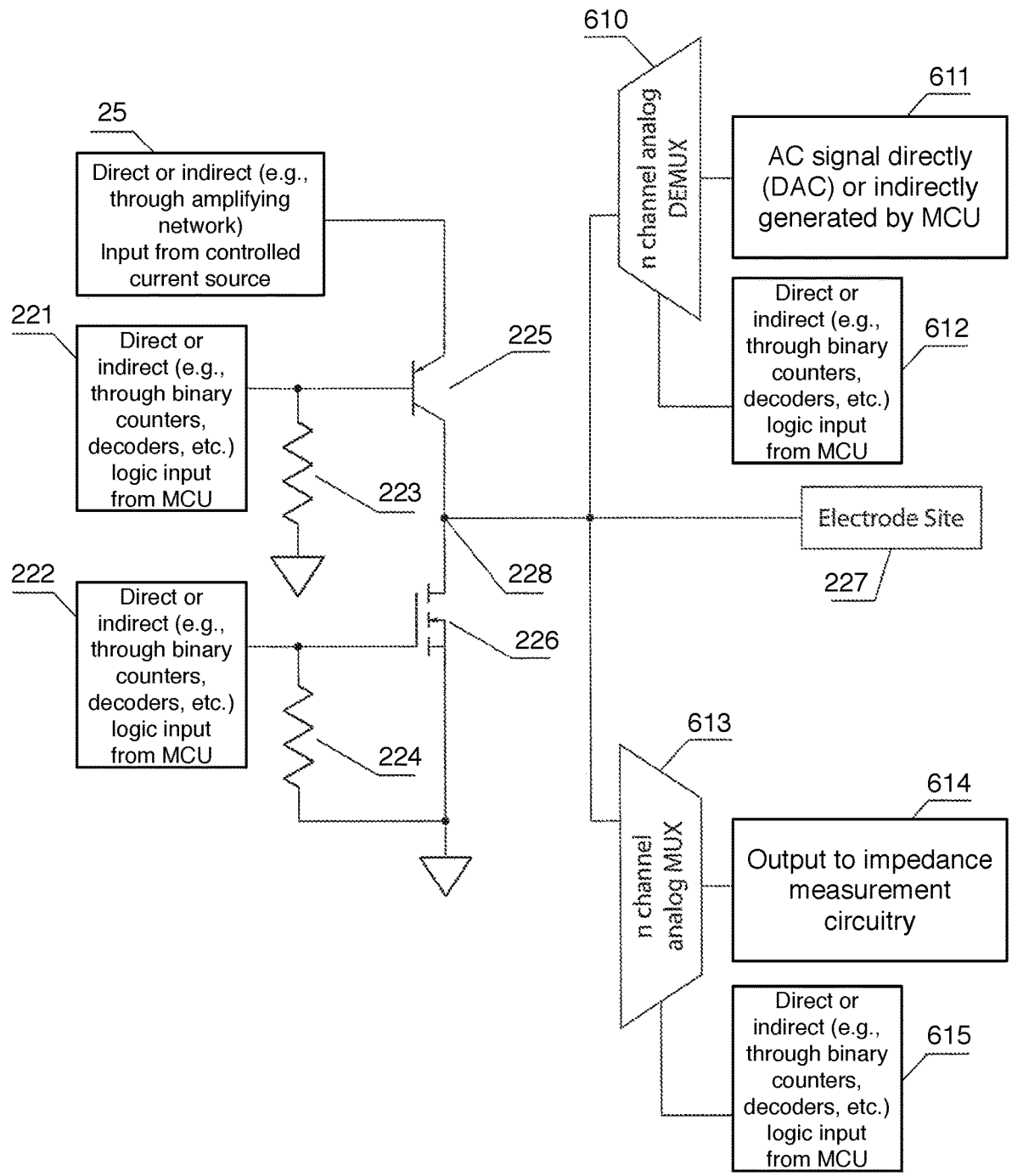
FIG. 8 is a circuit diagram depicting one embodiment of end stage(s) with impedance measurement functionality.

As shown in the exemplary implementation of FIG. 8, bone growth monitoring circuitry 16 can include end stages that address impedance monitoring. The exemplary end stage embodiment can comprise of a PNP bipolar transistor 225, a re-channel MOSFET 226, and two optional resistors 223 and 224 and may receive direct or indirect input from a controlled current source 25 which may determine the current amplitude flowing through a plurality of electrodes 116, and direct or indirect inputs 221, 222 from a microcontroller 113 determining the state (anode, cathode, non-conductive/passive) of electrode site(s) 227 connected to the shown end stage embodiment.

In the end stage implementation, the collector terminal 225 and the drain terminal 226 can be connected to one or more electrode sites 227. In addition, electrode site(s) 227 may receive a single input from a n channel (where n is the number of end stages) analog demultiplexer 610, and may give rise to a single output to a n channel (where n is the number of end stages) analog multiplexer 613. Analog demultiplexer 610 may receive one or multiple direct or indirect inputs 612 from a microcontroller 113 which can be used to select which of the n output channels will be connected to a single demultiplexer input channel. Additionally, in one embodiment, a microcontroller 113 may also directly or indirectly generate an input to a single demultiplexer input channel 611. Similarly, in the depicted embodiment, an analog multiplexer 613 may receive one or multiple direct or indirect inputs 615 from a microcontroller 113 which can be used to select which of the n input channels will be connected to a single multiplexer output channel. In one embodiment, the single multiplexer output channel can be connected to an impedance measurement circuitry 614.

Figure 9:
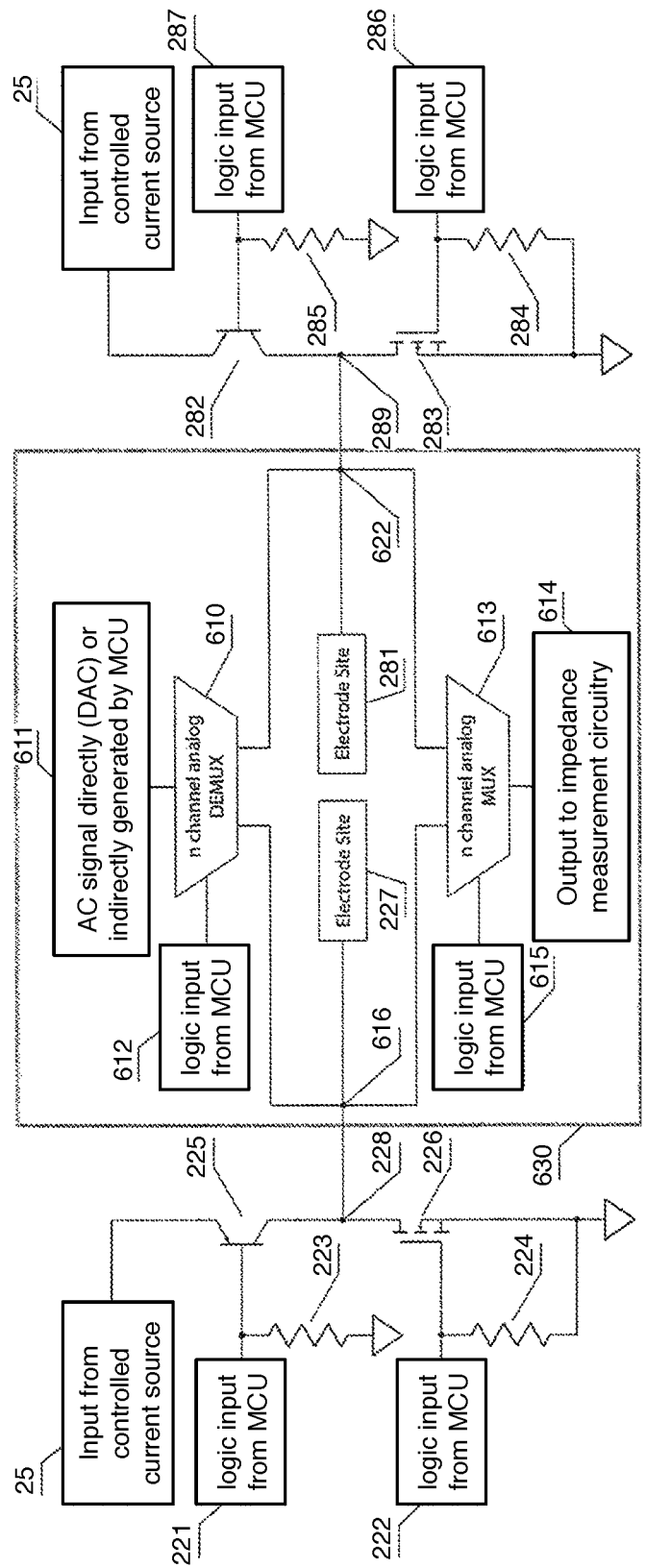
FIG. 9 is a circuit diagram depicting one embodiment of paired end stage(s) with impedance measurement functionality.

As shown in the exemplary circuitry implementation of FIG. 9, each end stage may receive a single input from a n channel analog demultiplexer 610 and may have a single connection to the inputs of an analog multiplexer 613. To test the impedance of the tissue between electrode sites 227 and 281, analog demultiplexer 610 may receive a direct or indirect input from a microcontroller 113 which may be used to set the internal state of analog demultiplexer 610 so that its input connects to its outputs connected to 227 or 281 and the analog multiplexer 613 may receive a direct or indirect input from a microcontroller 113 which may be used to set the internal state analog multiplexer 613 so that the input from the electrode sites 227 or 281 not connected to the input from analog demultiplexer 610 may connect to the output of the analog multiplexer 613. To avoid current from leaking through transistors on the end stages, each of any end stage(s) included the implantable component(s) can be adjusted to its passive state (MOSFETs gate input low, bipolar transistor base input high) during the impedance measurement procedure.

Figure 10:
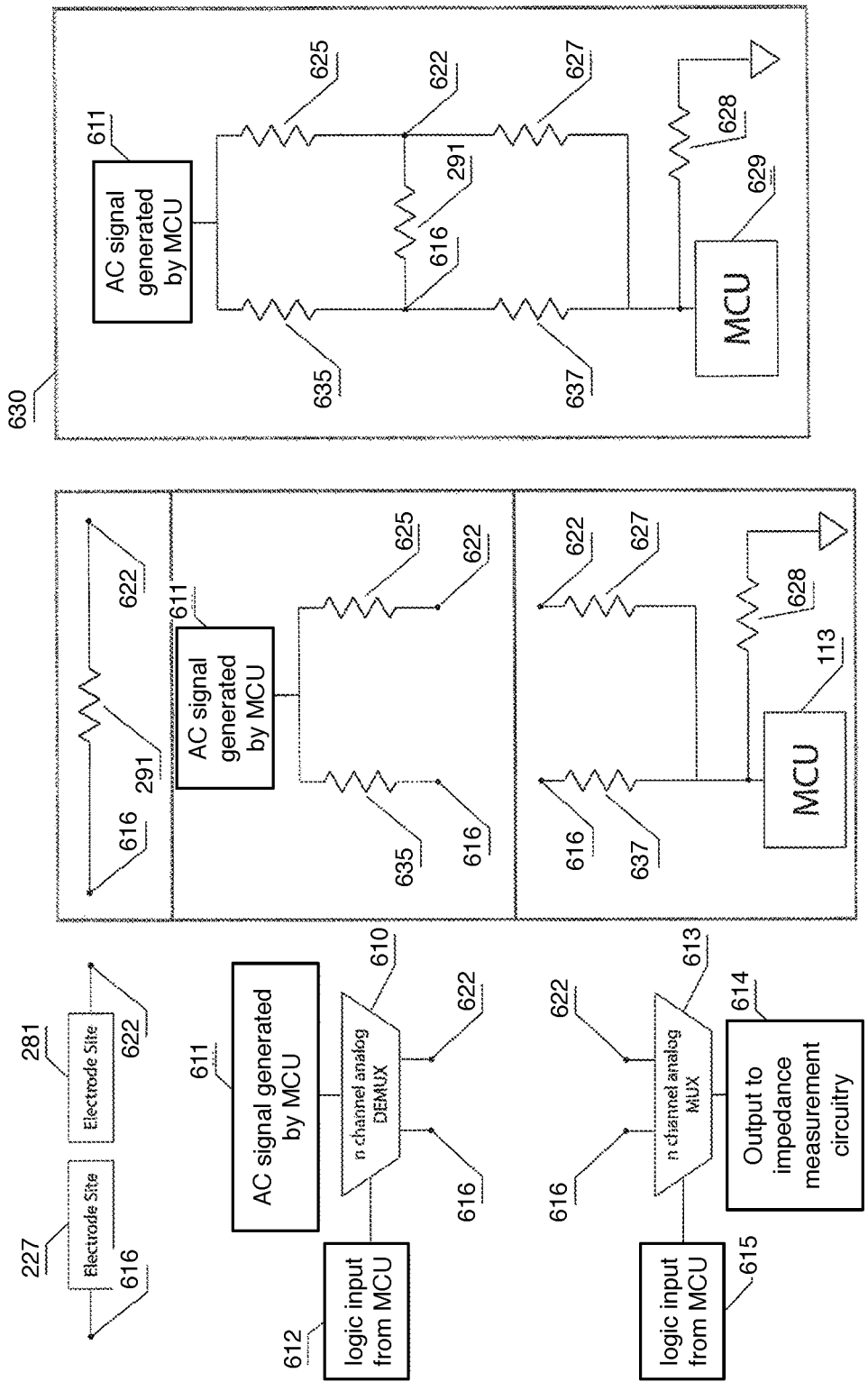
FIG. 10 is circuit diagram depicting how electrodes, tissue impedance, and one exemplary embodiment can be modeled.
Figure 11:
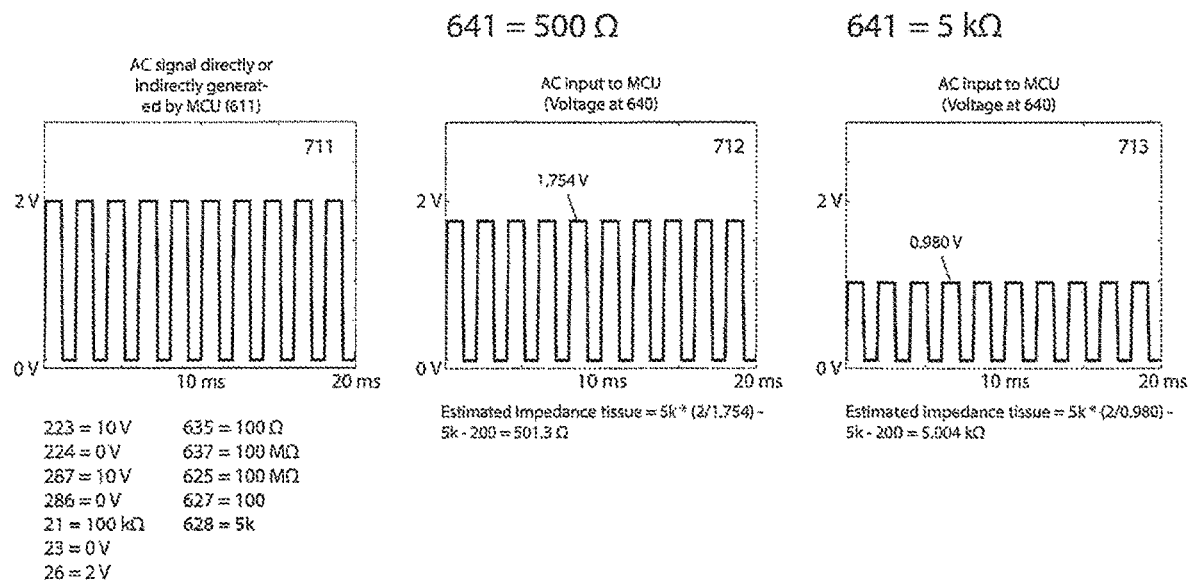
FIG. 11 is a set of SPICE based circuit simulations illustrating some functionality of one embodiment of end stage(s) with impedance measurement capabilities.

FIG. 10 is circuit diagram depicting how electrodes, tissue impedance and one example embodiment of the impedance measurement system that may constitute one component of the inventive medical implant system, can be modeled during the generation of the SPICE based circuit simulation results shown in FIG. 11.

FIG. 110, demultiplexer 610 can be modeled as an array of parallel resistors (635 and 625 for end stages shown in FIG. 10) connected from an AC source 611 (modeling a signal generated directly or indirectly by a microcontroller 113) to electrode sites. Similarly, multiplexer 613 can be modeled as an array of parallel resistors (637 and 627 for the end stages shown in FIG. 10) connected from electrode sites to an impedance measurement circuitry 614. The difference between connected and non-connected inputs and outputs can be modeled by assigning different resistances (100 MΩ for non-connected inputs and outputs and 100Ω for connected inputs and outputs) to resistors. Electrode sites 227 and 291 and the tissue between electrode sites 227 and 291 can be modeled using a resistor 291.

As shown in FIG. 11, simulations can be carried out on various impedance measurement functionality (such as those shown in FIG. 9 and FIG. 10) to show impedance measurement capabilities (using LTspice or other SPICE based circuitry simulations). During simulations, potentials at inputs 223/224/287/286 were set to 10/0/10/0 V, the resistance of resistor 21 was set to 100 kΩ, potentials at inputs 23/26 were set to 0/2V (setting the output constant current source embodiment shown in FIG. 16 to 0 µA). During simulations, connected channels were modeled using the connected and non-connected channel input impedances of 74HC4067 (NXP Semiconductors, Eindhoven, Netherlands) ~100Ω/100 MΩ. In addition, it was assumed that the internal state of n channel analog demultiplexer 610 was set up such that a AC signal 611 directly or indirectly generated by microcontroller 113 were connected to electrode 227 (resistance of resistor 635 was set to 100Ω while resistance of resistor 625 was set to 100 MΩ) while the internal state of n channel analog multiplexer 610 was set such that an input from electrode 281 was connected to an output to the impedance measurement system 614 (the resistance of resistor 637 was set to 100 MΩ while the resistance of resistor 627 was set to 100 MΩ). An impedance measurement system was modeled as an input to a microcontroller 113 and a single resistor 628 with a resistance of 5 kΩ. Simulated signals generated at node 640 in response to an input signal 711 for electrode/tissue impedances 641 of 500 Ω and 5 kΩ are shown in 712 and 713 respectively. For both modeled impedance values, the electrode/tissue impedance 641 can be calculated based on the amplitude of signals generated at node 640 using ohms law. As shown through the simulated measurements of FIG. 1i, the end stages shown in FIGS. 9 and 10 can be used to measure the impedance between any n−1 electrode pairs.

Additionally such impedance measurements may be mapped to location information based on which electrodes are used in reading a particular impedance measurement.

Figure 12:
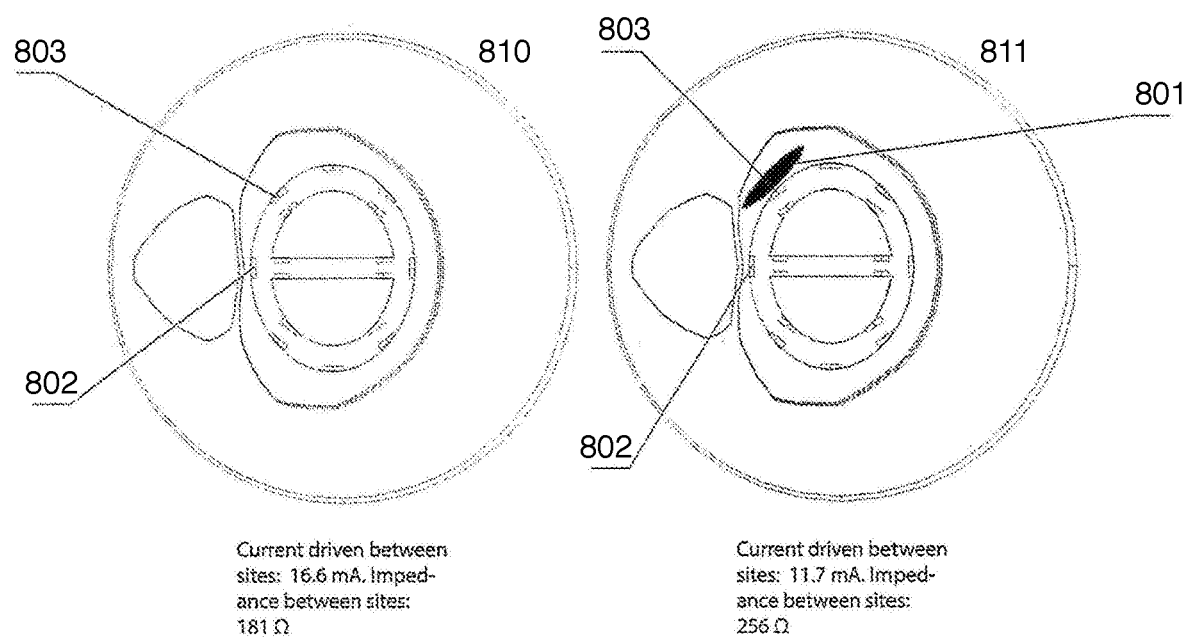
FIG. 12 is a schematic representation of measuring impedance changes resulting from bone mass formation in the fusion space.

As shown in FIG. 12, the implant component 3 can be used to measure impedance changes between two or more electrodes that results from an increase or decrease in bone mass in the fusion space of a spinal cage. In one exemplary simulation, a potential of 0 V and 3 V were assigned to single electrode sites 802 and 803, respectively. The amplitude of simulated current flowing between 802 and 803 was measured by integrating the surface current density over 802. The total current during simulation when no bone was present in the intervertebral canal 810 was 16.6 mA, which, according to ohms law, implies that the impedance between the two electrodes is 181Ω. The addition of an oval column of bone 801 (with a conductivity of 0.2 S/m2, approximately that of trabecular bone) in the position shown in 811 resulted in the amplitude of the current flowing between 802 and 803 decreasing to 11.7 mA, implying that the impedance between 802 and 803 increased to 256Ω. In summary, FIG. 12 illustrates that, for one embodiment of the inventive medical implant system where the implantable component(s) comprises partly of a spinal cage, it is possible to measure a change in impedance between two or more electrode resulting from an increased or decreased bone mass in the fusion space.

2.2 Non-Implantable Component

The non-implantable component 2 of a preferred embodiment functions to transmit power to an implantable component 3 and interface with the implantable component 3 for other forms of a control. The non-implantable component is preferably primarily designed to transmit power to the implantable component 3 accordingly the non-implantable component 2 can include a power source and transmitter circuitry. The non-implantable component 2 additionally includes a body or housing. The system may include a single non-implantable component 2, but may alternatively include a set of non-implantable components 2 which may operate cooperatively or independently. The non-implantable component may additionally include operational logic such that the non-implantable component 2 could automatically manage operation of the implantable component 3. Alternatively or additionally, the non-implantable component 2 may be used to relay user specified directives to the implantable component 3.

As shown in the exemplary embodiment of FIG. 3, a non-implantable component(s) 2 may include circuitry supporting wireless communication with user interface components 1. In some embodiments, the non-implantable component(s) 2 may also include circuitry to enable non-implantable component(s) 2 to power and communicate with implantable component(s) 3 using induction, electrical radiative coupling such as RF irradiation, ultrasound or IR. In various embodiments, non-implantable component(s) 2 may include a power source such as a battery used to power all circuitry included in non-implantable 2 and implantable component(s) 3 and provide the energy necessary to introduce osteoinduction or osteolyis in the fusion space by electrical stimulation delivered through implantable component(s) 3. Non-implantable component(s) 2 may also include circuitry to store/process received data, store/process received control signals, directly or indirectly control the state of circuitry included as part of non-implantable component(s) 2 and determine the content and format of signals sent to user interface components 1 and/or implantable component(s) 3.

Figure 13:
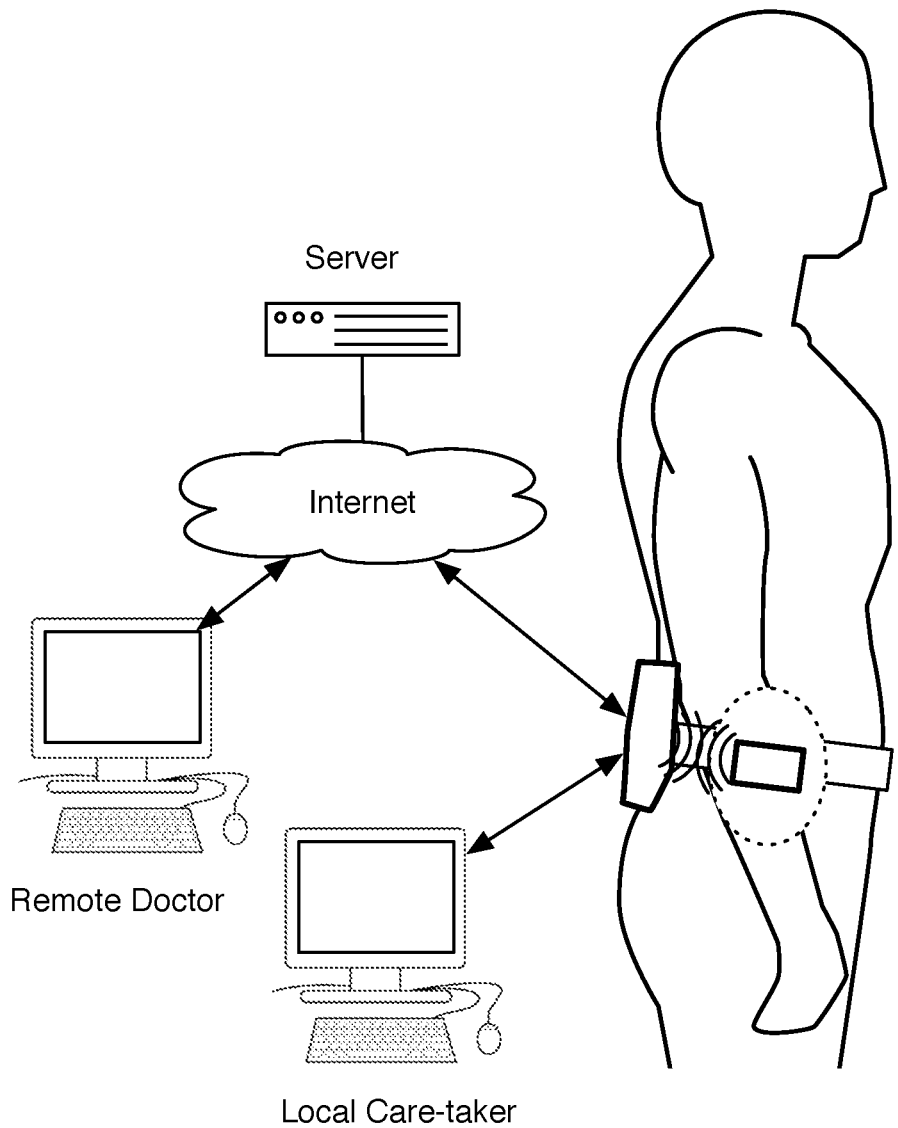
FIG. 13 is a schematic representation of a network of non-implantable components.
Figure 14:
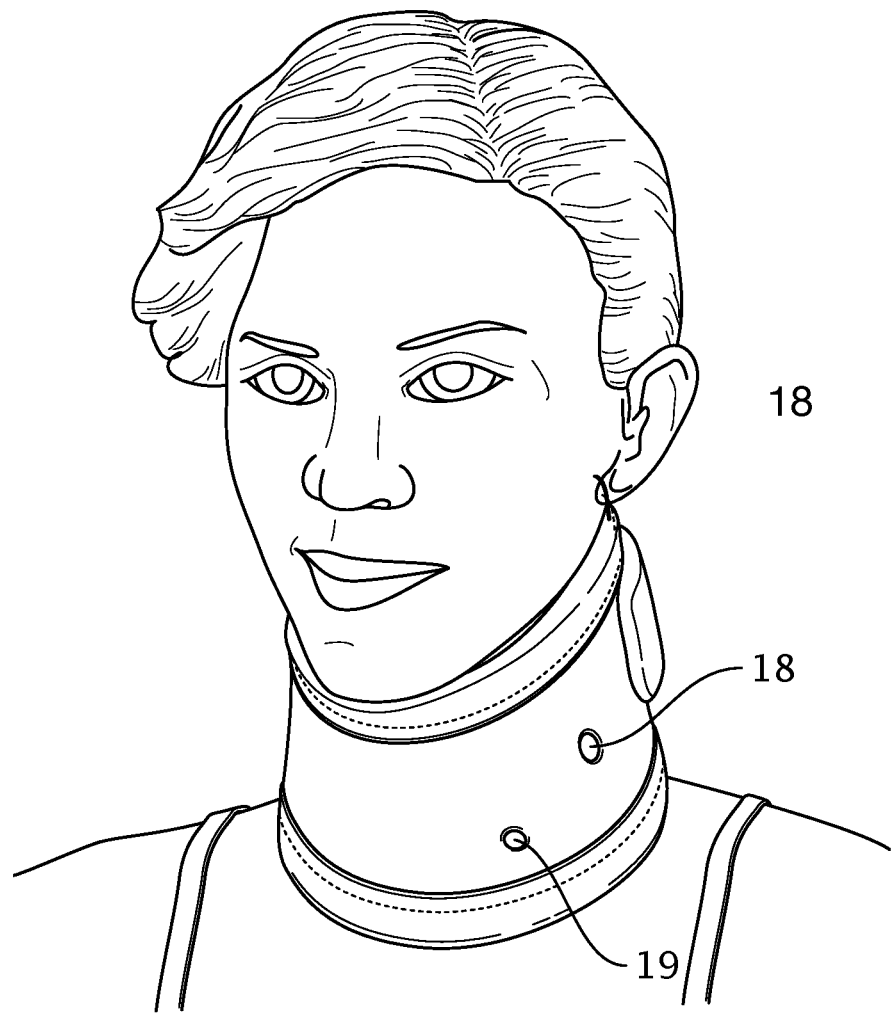
FIG. 14 is a schematic representation of an exemplary body of a non-implantable component during use.

The non-implantable component body functions to house the components of the non-implantable component. In one implementation, the non-implantable component may be housed in a medical device body, such as a lumbar corset or a cervical collar. Preferably, the body of the non-implantable component 2 can be worn in close proximity to the implantable device as shown in FIG. 13 Electrical leads may be provided to connect the power source to the transmitter circuitry. As shown in FIG. 14, the body could be a non-implantable cervical collar that includes a power source 18, and transmitter circuitry 19. Transmitter circuitry 19 may be operably coupled to power source 18 by leads, and may be effective for converting electric power from the power source to an electromagnetic field. Other suitable form factors of the non-implantable body may alternatively be used. Preferably, the non-implantable component body enables the transmitter circuitry to be physically positioned so as to properly transmit power wirelessly to the implantable component 3.

As shown in FIG. 4, the Power source 103 can function to power all circuitry included in the non-implantable 2 and implantable component(s) 3 and provide the electrical charge used to introduce osteoinduction or osteolyis in the fusion space. Energy used to power non-implantable component(s) 3 may be provided directly from power source 103 through wires, PCB traces or leads. Energy used to power the implantable component(s) and stimulate tissue may be provided from the power source 103 using induction, RF irradiation, ultrasound IR, and/or any suitable wireless power transmission approach. In various implementations, the power source 103 may provide DC power to an oscillator circuit 105 which is effective in transmitting some of this power to the implantable component(s) by using some of it to generate narrowband AC oscillations within a transmitter coil 108 which can generate oscillating electrical signal over an receiver coil 109 (part of the implantable component(s)) through inductive coupling. In other implementations, power source 103 may be used to generate narrowband AC signals over a RF antenna (such as a dipole antenna), an ultrasonic transducer, an IR emitter or another transmitter suitable for wireless energy and/or data transfer. The transmitted power signal preferably couples to a corresponding receiver on the implantable component 3. Any suitable type of antenna, transducer, or power transmission/receiver mechanism may be used.

An AC signal generated over receiver coil 109 may be converted into DC signals using a rectifying circuitry 107. If at any instance, the power of induced DC signals is higher than the sum of the power consumption of all implantable component(s) and any power used to stimulate tissue, the excess power can be stored using capacitor(s). If, at any instance, the sum of the power consumption of all implantable component(s) and any power used to stimulate tissue exceeds that provided the by power source 103 wirelessly, charge stored within capacitor(s) can be used to partially or fully compensate this discrepancy. In some implementations, charge stored in capacitor(s) may fully power the implantable component(s) and/or stimulate tissue in during periods where the transmitter is not actively transmitting power from a power source 103. According to one embodiment, power source 103 may comprise one or more rechargeable and/or non-rechargeable batteries. The power source may alternatively be a power supply that connects to a wall outlet or other external power source.

The transmitter circuitry 19 may include transmitter output circuitry, and may also optionally include transmitter control circuitry and/or transmitter communication circuitry. The transmitter circuitry may be effective for converting electric power from the power source 18 to a modality that can be transmitted wirelessly to an implantable component (e.g. using Induction, RF Irradiation, IR, ultrasound etc.), and may also be effective for managing communications between the various components. The transmitter output circuitry could be effective for generating the wireless power/communication signal, which may include generating an electromagnetic field, acoustic field, or other suitable forms of radiative signal. The transmitter output circuitry could include the transmitter coil, the ultrasound inducer, RF antenna, IR transmitter, or other suitable component used in transmitting the wireless power signal. The transmitter control circuitry can function to control one or more characteristics of the electromagnetic field generated by the output circuitry. The transmitter control circuitry can create digital signals for turning oscillations in the transmitter coil on and off and may be used by the transmitter communication circuitry.

The transmitter communication circuitry may allow the transmitter circuitry to communicate with the implantable component 3. The transmitter communication circuitry can be used in communicating with the implantable component, but can additionally decode or interpret signals received from the implantable component. The transmitter communication circuitry or another communication system may also communicate with user interface component(s), secondary computing devices (e.g., a smart phone, computer, or remote server) and/or other non-implantable components 2. One or more portions of the transmitter communication circuitry may be wireless.

In one embodiment the transmitter circuitry may comprise a class-E transmitter circuit generating an oscillating electric current within a transmitter coil that induces a potential over the tuned receiver coil located within implant through inductive or other wireless coupling.

As previously indicated, to allow physicians and technicians to interact with the implant the non-implantable component may include a wired, or alternatively wireless, communication capability. In one potential embodiment this additional communications capability may be achieved by including Wi-Fi® or Bluetooth® capability to the non-implantable component. This way, a potential user may interact the system through a user interface software application running on a computer, tablet, or smartphone with Wi-Fi or Bluetooth capability as shown in FIG. 13. Through the UI, physicians or technicians may adjust the setting of the stimulator (current amplitude, choice of channels, stimulation frequency if AC is used, frequency of impedance measurements etc.) based on feedback from imaging or from the implant itself. If the feedback is provided by the system itself, the output may be adjusted by a preprogrammed algorithm.

As shown in the exemplary implementation of FIG. 4, a microcontroller 101 can be used to send and receive signals from user interface components 1 through a wireless module 102, may control the output of an oscillator circuit 105 directly or through inputs to an oscillator control circuit 104, may monitor the state of power source 103, may receive signals from the implantable component(s) 3 through an induction coil 108 or other receiver, and may send signals to the implantable component(s) 3 by directly or indirectly controlling the output of an oscillator circuit 104. In the depicted embodiment, impedance measurement data may be received by a tuned air core receiver coil 108 as pulsed AC oscillations. In the shown embodiment, pulsed AC oscillations in a receiver coil 108 may be converted into DC current using rectifying circuitry 107. In one embodiment, rectifying circuitry 107 functions as an envelope detector and the envelope of received AC signals may carry impedance measurement data which may be stored and/or processed by a microcontroller 101 and/or transmitted by a microcontroller 101 to a user interface 1 through a wireless communications module 102. In the depicted embodiment, oscillator control circuitry 104 may control the state of an oscillator circuit 105 such that an AC oscillatory current may be actively generated or not actively generated within a transmitter coil 106.

A user interface component can function to provide a mechanism for human interaction with the implantable component 2. The user interface component can be used for receiving impedance and bone growth data, stimulation logs/reports, implantable device settings, implantable device diagnostics, and/or other suitable information. The user interface component may additionally or alternatively be used for receiving user input on operation changes to the implantable component 3. User interface components 3 may comprise of a computer device, such as a workstation, laptop, tablet, or smart phone, which runs a software application and a module which allows wireless communication through some wireless communication technology such as Wi-Fi or Bluetooth. In another variation, the non-implantable component 2 may communicate with a remote server hosted in the cloud. The software application may enable a desired user to monitor system status, monitor impedance measurement data, and change various system parameters including stimulation current amplitude and electrode configuration, among other functions.

3. Exemplary System Component Implementations

The system may be implemented with a variety of system level design approaches, using various electronic elements or circuit design approaches.

Figure 15:
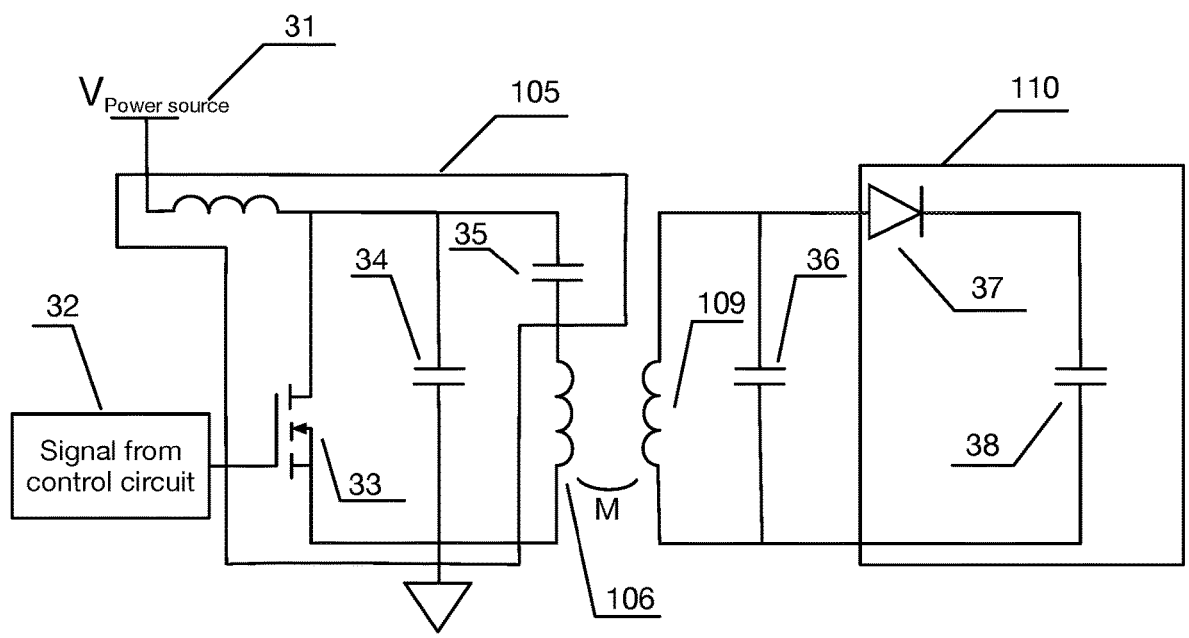
FIG. 15 is circuit diagram of an exemplary a transmitter-receiver circuit.

As shown in FIG. 15, one exemplary implanted and non-implanted implementation of communication between an implantable component 3 and a non-implantable component 2 can include an oscillator circuit 105, transmitter coil 106, receiver coil 109, and rectifying circuit 110 according to one embodiment where the oscillator circuit 105 is a type of class-E oscillator circuit and the rectifying circuit is a half wave rectifier 110. As shown in FIG. 15, a power source 103 can provide DC input to the oscillating circuit, which may generate a narrowband AC oscillatory current through a transmitter coil 106. Input 32 from the oscillator control circuitry 104 may turn the circuits switching transistor 33 on and off at a frequency similar to the resonant frequency of the oscillator circuit 105. Current in a transmitter coil 106 can give rise to a magnetic field, which in turn may induce a potential over a receiver coil 109. A potential over receiver coil 109 may be determined by multiple factors including the mutual inductance between the transmitter 106 and receiver coils 109, the relative and absolute inductance of transmitter 106 and receiver coils 109, and the amplitude and frequency of current over transmitter coil 106. A high coupling may be achieved in the exemplary implementation of FIG. 15 if receiver coil 109 is tuned to the resonant frequency of oscillator circuit 105, receiver coil 109 can be tuned by adjusting the capacitance of the tuning capacitor 36. Rectifier circuitry 110 may comprise of a single diode 37 in series with a single capacitor 38 forming a half wave rectifier as show, an full wave rectifier, or any other type of single or multi stage rectification system. As mentioned above alternative wireless power and communication approaches may be used including alternative forms of electrical radiative coupling such as RF irradiation, ultrasound, infrared radiation (IR), and/or any suitable wireless communication/power transmission approach.

Figure 16:
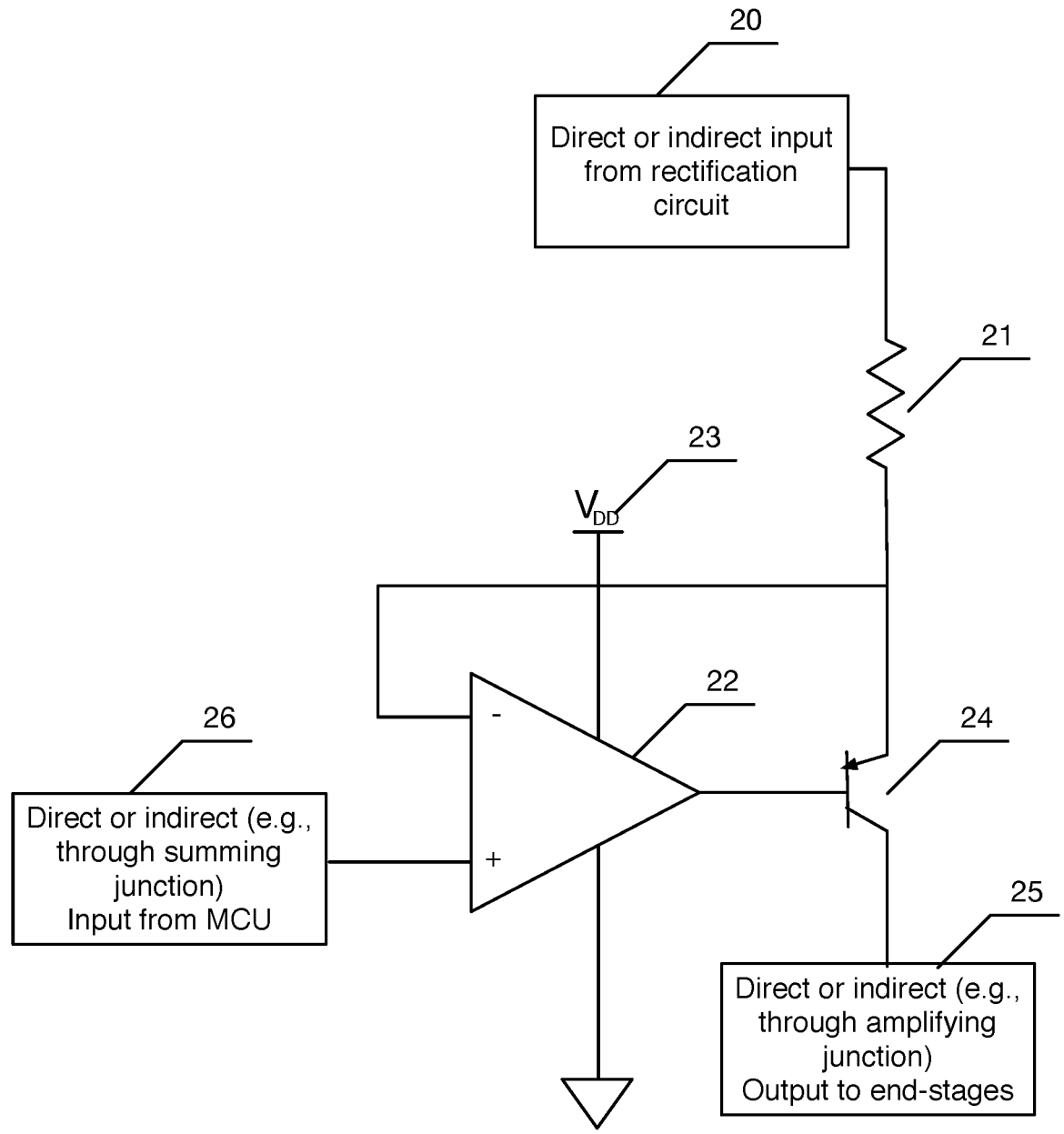
FIG. 16 is circuit diagram of an exemplary controllable current source.

As shown in FIG. 16, an implantable device may use a controlled constant current source 111 to end stages of the implantable component 2. In one example, the controlled current source 111 comprises of an OP-amp 22, a resistor 21, and a PNP bipolar transistor 24. Under ideal operating conditions, the amplitude of current, which may flow directly or indirectly into end stage(s) 25, can be adjusted by adjusting the potential difference between an input emanating directly or indirectly from a microcontroller 26 and an input emanating directly or indirectly from rectification circuitry 20 and/or by adjusting the resistance of resistor 21. Assuming a constant voltage at the input emanating directly or indirectly from rectification circuitry 20 and a fixed resistance of resistor 21, it may be possible to adjust the current amplitude flowing directly or indirectly to the end stages 25 by adjusting the voltage of the signal set directly or indirectly by a microcontroller 26.

Figure 17:
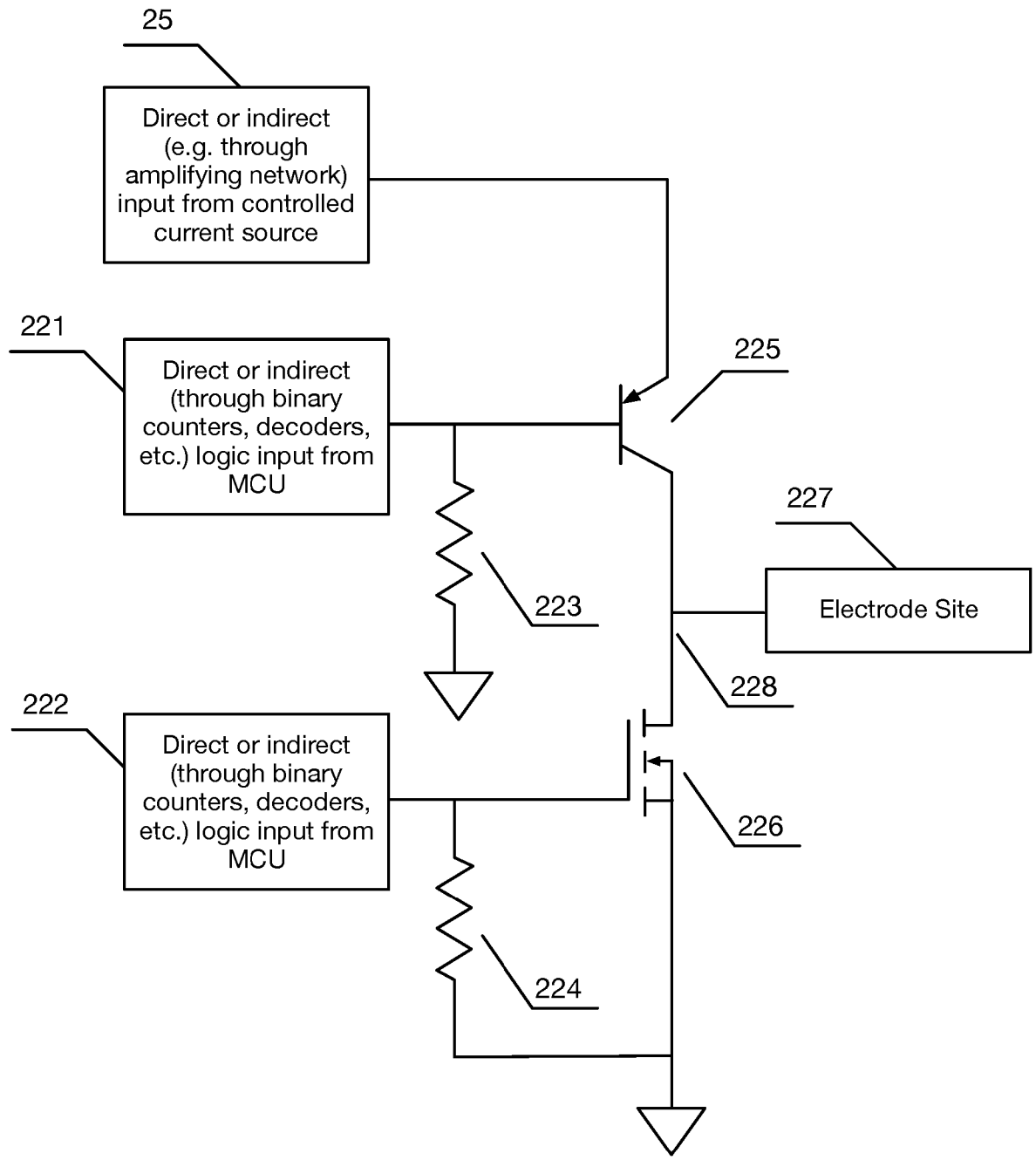
FIG. 17 is circuit diagram of exemplary end stage(s)

FIG. 17 is a circuit diagram of one potential embodiment of end stage(s) 114. The shown end stage embodiment comprises a PNP bipolar transistor 225, a n-channel MOSFET 226, and two optional resistors 223 and 224 and may receive direct or indirect input from a controlled current source 25 which may determine the current amplitude flowing through a plurality of electrodes 116, and direct or indirect inputs 221, 222 from a microcontroller 113 determining the state (anode, cathode, non-conductive/passive) of electrode site(s) 227 connected to the shown end stage embodiment.

Figure 18:
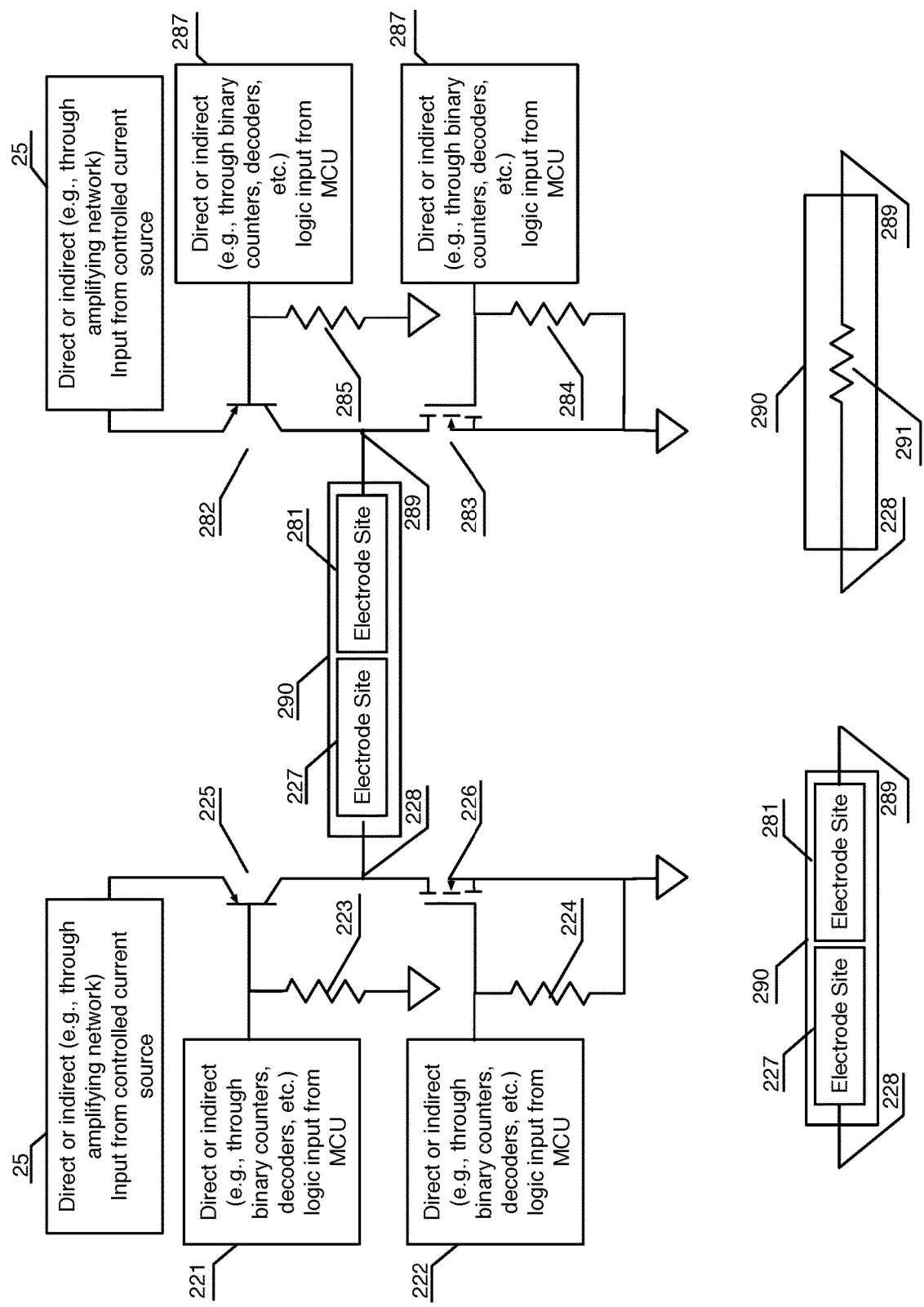
FIG. 18 is circuit diagram depicting an example of paired end stage(s) and a representation of how electrodes and tissue impedance can be modeled during the stimulation.

FIG. 18 shows a circuit diagram representation of one embodiment of two paired end stages, each connected to a single or multiple electrode site(s). The figure also includes an illustration of how electrode and tissue impedance can be modeled to generate the SPICE based circuit simulation results shown in FIG. 19. Specifically, electrode sites 227 and 291 and tissue between electrode sites 227 and 291 can be modeled using a resistor 291 in the manner shown by grey rectangle 290.

Figure 19:
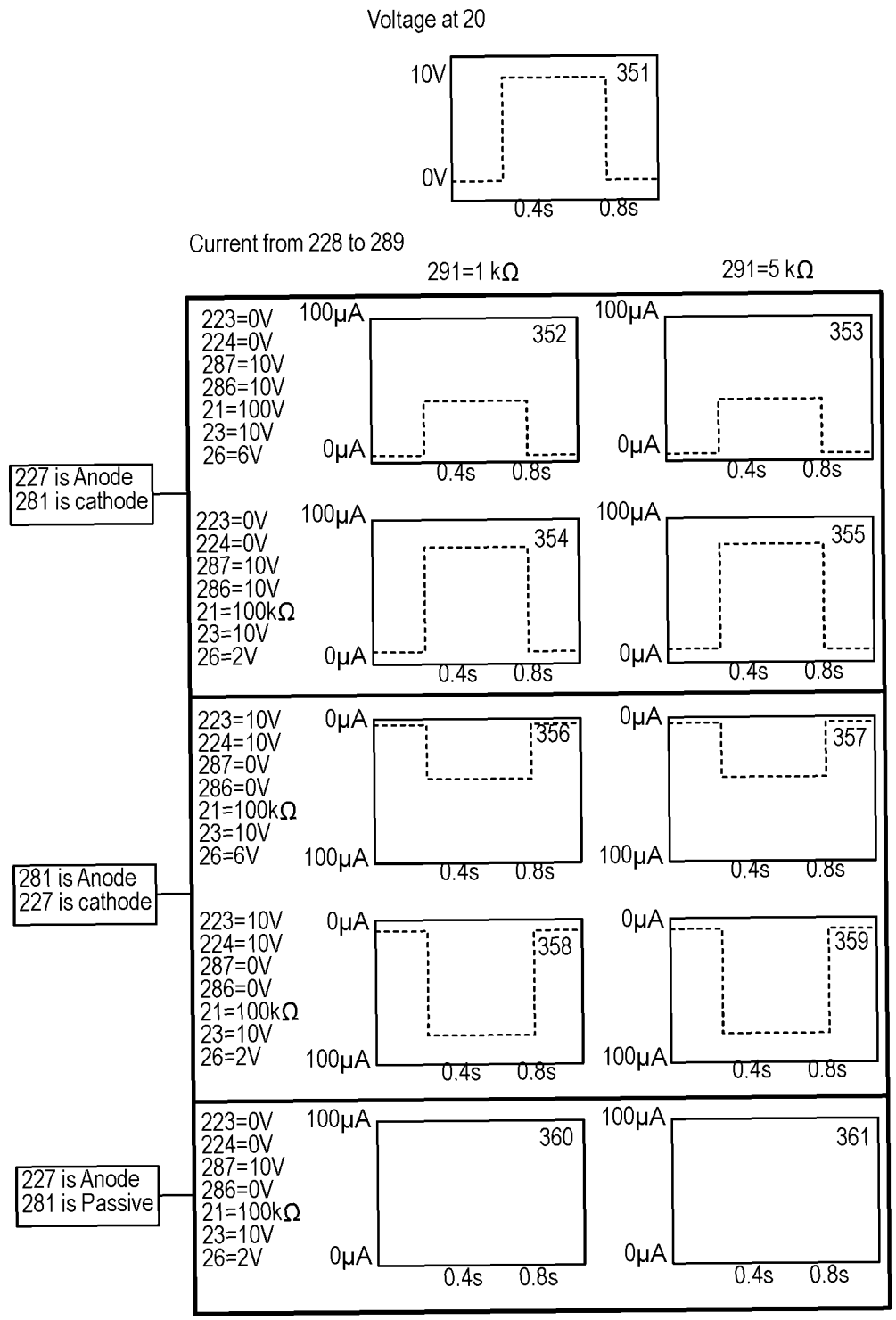
FIG. 19 shows results from a SPICE based circuit simulation illustrating functionality of an exemplary end stage(s) and a controllable current source.

FIG. 19 shows results from a SPICE based circuit simulation illustrating some functionality of the end stage(s) depicted in FIG. 18 and the controllable current source depicted in FIG. 16. Op-amp 22 can be modeled using LT1001S8, bipolar transistor 24 can be modeled using 2N4403 (Fairchild), bipolar transistors 225 and 282 can be modeled using A06408 (Alpha and omega). During the simulation the resistance of 21 was set to 100 kn. Simulations were carried out for two different electrode/tissue impedances 291: 1 kΩ and 5 kΩ. Input voltage 20 was modeled as a 500 ms long 10 V, square pulse. 352-361 shows the current flowing from node 228 to node 289 in response to the input voltage for the described circuit model. When inputs 223/224/287/286 were set to 0/0/10/10 V, respectively, current with an amplitude determined by the input at 26, flowed from electrode 227 to electrode 281 (352-355). The amplitude of the current was not impacted by tissue impedance (compare 352 to 354 and 354 to 355) for the modeled tissue/electrode impedances (1 kΩ and 5 kΩ). When the inputs of 223/224/287/286 were set to 10/10/0/0 V, respectively, the direction of the current was reversed, flowing from electrode 281 to electrode 227 (356-359). When the inputs of 223/224/287/286 were set to 0/10/0/0 V, respectively, no current flowed through the end stage connected to electrode 281 resulting in no current flow between the two electrodes (360-361). In summary, FIG. 19 shows how one embodiment (shown in FIGS. 17-18) of end stages can set the state (anode, cathode or non-conductive/passive) of a plurality of electrodes 116. FIG. 19 also shows how one embodiment of controlled current source shown in FIG. 16 can be used to adjust the amplitude of current flowing between a plurality of electrodes 116 and that the amplitude of said current can be adjusted based on the potential difference (but not the electrode/tissue impedance 291) between the input emanating directly or indirectly from a microcontroller 26 and the input emanating directly or indirectly from rectification circuitry 20 and the resistance of 21.

4. Method for Using a Dynamic Stimulation Implant System

Figure 20:
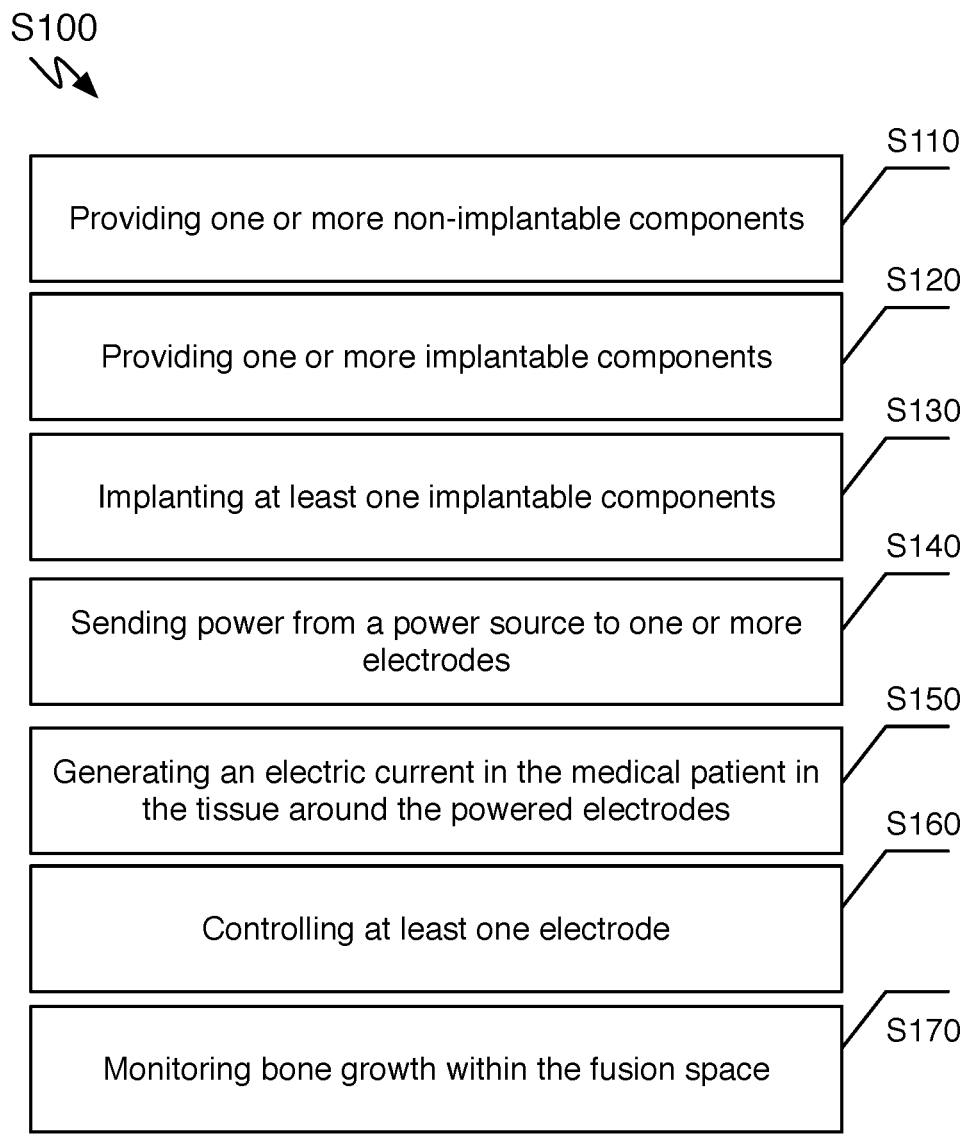
FIGS. 20-23 are flow diagrams of methods of a preferred embodiments.

As shown in FIG. 20, a method S100 for using a dynamic stimulation implant system of a preferred embodiment can include: providing one or more non-implantable components S110, providing one or more implantable components S120, implanting at least one implantable components in a medical patient S130, sending power from a power source to one or more electrodes S140, generating an electric current in the medical patient in the tissue around the powered electrodes S150, and controlling at least one electrode S160.

The non-implantable components provided in block S110 can include a power source, transmitter circuitry and/or any of the elements described above or alternative elements.

The implantable components of block S120 can include a medical implant body, implant circuitry, and a plurality of electrodes. The set of electrodes are preferably integrated into the body of the implantable component, and the implant circuitry includes control circuitry to enable electrical interaction with the fusion region around the implantable component. The implant circuitry can include: implant receiver circuitry effective for converting energy emitted by the transmitter to an electrical current. The implant control circuitry is preferably effective to control one or more of said electrodes with respect to whether electric current is flowing through the electrode or is not flowing through the electrode, and, when current is flowing through the electrode, with respect to one or more characteristics of the current flowing through the electrode. The plurality of electrodes can be connected directly or indirectly to the implant circuitry and is effective for providing an electric current to a space adjacent said electrode. In one variation, providing an implantable component can include providing a standalone medical implant with integrated circuitry. Such a medical implant is preferably in a form factor emulating the structural properties of a medical implant, such as a spinal cage used in spinal fusion. In another variation, providing an implantable component can include providing an implantable component that can be used in combination with a medical implant device. Accordingly, providing an implantable component S120 can include coupling a dynamic stimulation implantable component to a static implant device. In one variation coupling can include adhering the implantable device to a medical implant device. Adhering the implantable device can include using adhesives, using mechanical coupling (e.g., stretching the implantable component around a medical implant device or inserting the implantable component within a medical implant device). In another variation, coupling can include mechanically fixturing a dynamic stimulation implantable component to a static implant device through a pressure fit, mechanic locking mechanisms, fasteners, magnets, or other suitable fastening approaches.

Sending power of Block S140 functions to transmit energy from the non-implantable components to an implantable component. The received energy is then used in generating an electric current in the medical patient in the tissue around the powered electrodes S150. Controlling the electrode can function to control the flow of electric current through the electrode and to control one or more characteristics of the flowing current (e.g., polarity, current density, etc.) so as to promote osteoinduction and osteolysis in the surrounding tissue region.

In one aspect of the present invention the medical patient is a patient being treated for a spine condition, and the medical device is a spine cage. In that method, electric current may be provided in an amount and for a time effective to stimulate measurable bone growth in a desired fusion space immediately adjacent or near to the implant.

One aspect of the method S100 also includes monitoring bone growth within the fusion space S110. Such monitoring may include driving AC signals between a pair of electrode sites and measuring the impedance of the tissue located between the two pairs. The method may be used to create an impedance profile of the entire fusion space, and the impedance profile may be used to monitor the degree of spinal fusion achieved. The implant control circuitry may additionally include circuitry for receiving the impedance profile, and for using the impedance profile information to turn channels off or on, or change their polarities. The impedance profile may also be used to increase or decrease the output of the stimulator.

5. Method for Dynamically Stimulating with an Implantable Device

Figure 21:
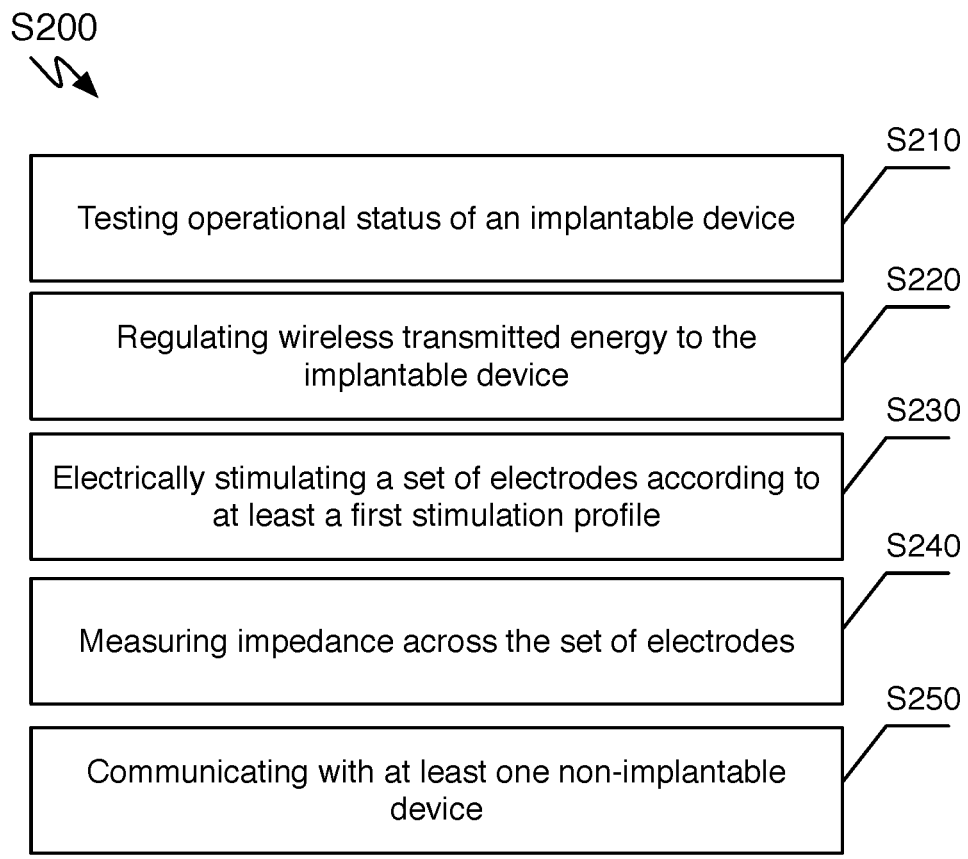

As shown in FIG. 21, a method S200 for dynamically stimulating a patient through an implantable device of a preferred embodiment can include regulating wirelessly transmitted energy to the implantable device S220 and electrically stimulating a set of electrodes according to at least a first stimulation profile S230. In a first variation, the method S200 can additionally include measuring impedance across the set of electrodes S240. As another variation, the method S200 can additionally include communicating with at least one non-implantable device S250. As yet another variation, the method S200 can additionally include testing operational status of an implantable device S210. The method S200 can be used in combination with methods and/or systems described herein or alternatively used with other system implementations.

Figure 22:
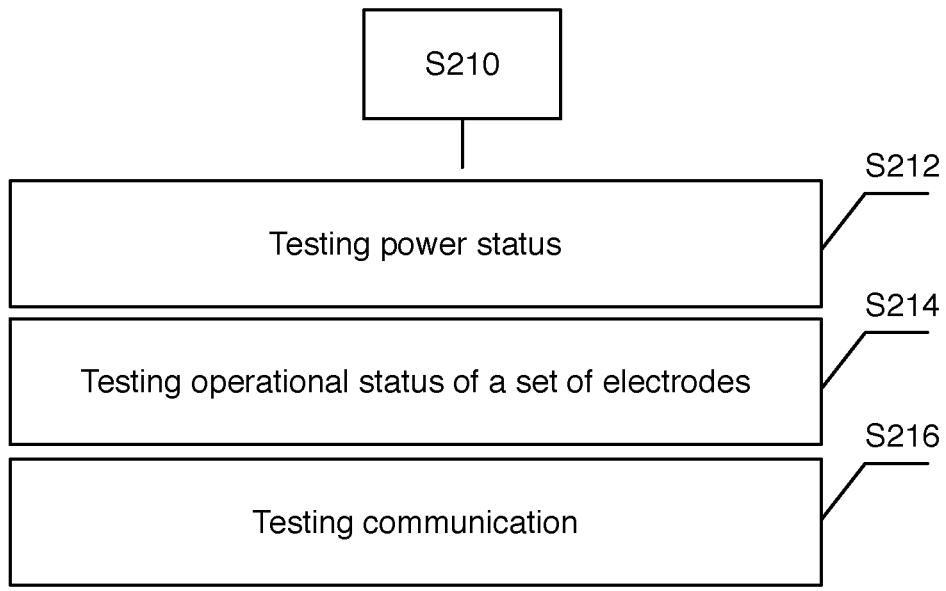

Block S210, which includes testing operational status of an implantable device, functions to perform diagnostics on the implantable component. Testing operational status can be performed at any suitable time. In one embodiment, a testing unit can be used to test the operational status of the implantable device prior to use in a surgical operation. For example, the implantable component could be inserted into the testing unit, and diagnostics mode could be triggered. Additionally or alternatively, testing operational status can be performed after having been surgically inserted into the patient. Testing operational status is preferably performed periodically. Testing operational status can include a set of different test, and more specifically, the various tests may be periodic testing at varying intervals and conditions. Testing operational status can include testing power status S212, testing operational status of a set of electrodes S214, and testing communication S216 as shown in FIG. 22.

Testing power status S212 functions to verify that sufficient energy is available to the implantable device. In one variation, testing power status S212 checks the condition of a temporary power storage unit. Various functionality of the implantable device may be available based on the amount of power. In another variation, testing power status S212 can include coordinating transmission of power from a non-implantable device and the received power at the implantable device, which may include cycling the non-implantable device through set of different modes of power transmission, measuring the power status during the set of different modes, and communicating power status results to the non-implantable device. Such power transmission coordination can function to identify a preferred power transmission mode based on the current condition. The conditions may vary based on the individual (e.g., the size/weight of the patient), the positioning of the non-implantable device, the material of the clothes, and/or other conditions. The implantable device will likely have a limited amount of energy storage if any, and so achieving at least a minimum power status can be important. Similarly, a non-implantable device may be operating off of a battery and will similarly benefit from conserving power. As such transmitting within a particular power window can work towards prolonging battery life.

Testing operational state of a set of electrodes S214, functions to verify the set of electrodes are operational. Testing operational state of the set of electrodes preferably comprises cycling through the set of electrodes and verifying that an expected impedance range can be detected during use of each of the electrodes.

Testing communication S216 can function to verify that data is properly received and/or transmitted. Testing of communication can include sending test messages between the implantable device and the non-implantable device. Such tests may involve the implantable device sending a test message to the non-implantable device, the non-implantable device receiving the message and transmitting a confirmation message back to the implantable device, which includes the original test message. The implantable device can verify that the confirmation message correctly includes the original test message. Other suitable communication tests can additionally be performed.

Block S220, which includes regulating wirelessly transmitted energy to the implantable device, functions to operate the implantable device within a particular power threshold. Regulating wirelessly transmitted energy can include monitoring power level at the implantable device. Monitoring power level may be substantially similar to testing power delivery, and in some implementations may be the same process. Regulating can include amplifying, converting between alternating and direct current, filtering power signal, and temporarily storing power. Additionally, regulating wirelessly transmitted energy can include communicating power status to the non-implantable device and at a non-implantable component, augmenting transmission of energy. Augmenting transmission energy can include altering the magnitude or intensity of power transmission and/or changing the power signal pattern. In a variation where directionality of transmission can be controlled, augmenting transmission of energy can include altering transmission directionality.

Figure 23:
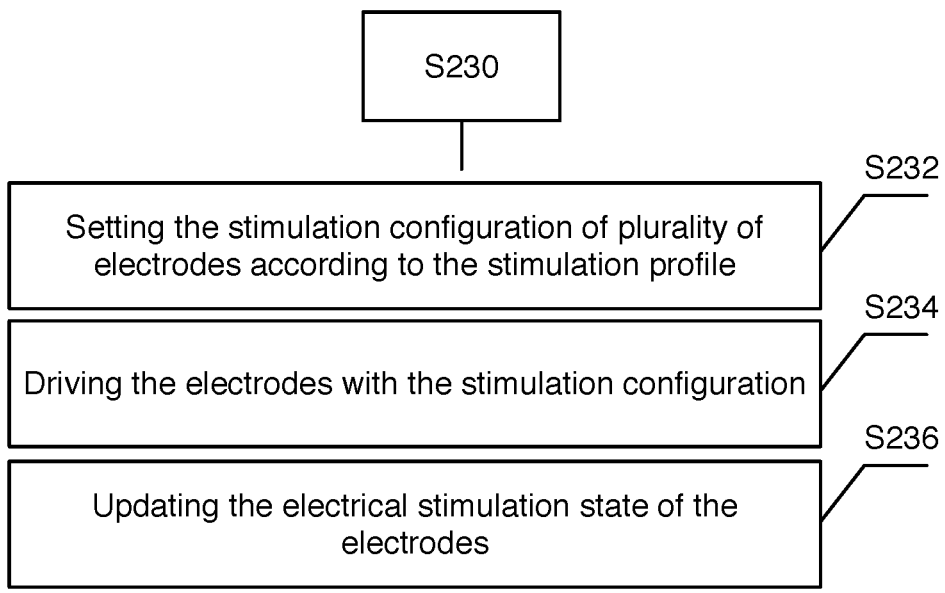

Block S230, which includes electrically stimulating a set of electrodes according to at least a first stimulation profile, functions to drive the electrodes so as to promote or deter bone growth in the vicinity of the implantable device. Electrically stimulating preferably involves controlling the current driven through various areas of the tissue near the implant (e.g., the spinal fusion region). Electrically stimulating a set of electrodes can include setting the stimulation configuration of plurality of electrodes according to the stimulation profile S232 and driving the electrodes with the stimulation configuration S234 as shown in FIG. 23.

Setting the stimulation configuration can include setting the electrode stimulation state and/or the potential magnitude. Stimulation state can include active/non-active state, polarity (e.g., anode or cathode if active), set current/voltage magnitude, a current/voltage signal if used, and/or any suitable characteristic of how current flows through the electrode when active. The stimulation configuration additionally involves determining the mapping of electrode states (i.e., how the set of electrodes are stimulated as a group). Different electrodes can be driven at different settings to create a different net effect. The stimulation profile can be automatically determined within the implantable device, on the non-implantable device, on a remote computing device in communication with the non-implantable device, or based on user specified instructions.

Figure 24A:
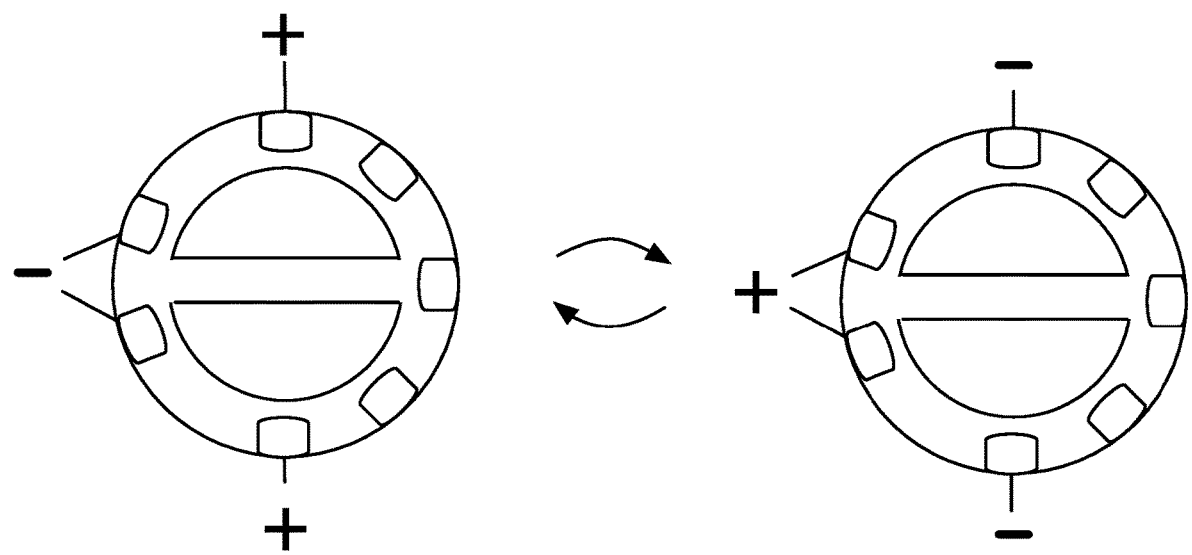
FIGS. 24A and 24B are schematic representations of updating the electrical stimulation of a set of electrodes.
Figure 24B:
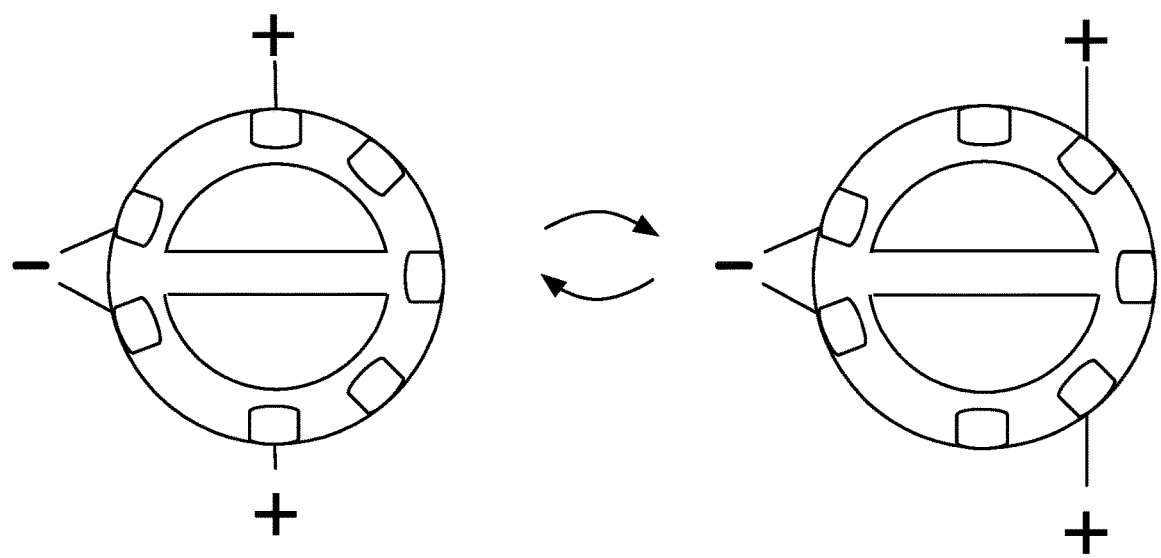

Electrically stimulating a set of electrodes can additionally include updating the electrical stimulation state of the electrodes S236, which functions to adjust the stimulation based on the conditions. Bone growth depends on the conditions, but S236 can enable the stimulation to be changed to retarget the induced osteolysis or osteoinduction regions. For example, during a first instance, the set of electrodes are driven in a first electrical stimulation state, and in second state, the set of electrodes are driven in a second electrical stimulation state as shown in FIGS. 24A and 24B. The electrical stimulation state is preferably updated according to a new stimulation profile that targets different effects. In the first state a first stimulation profile can be used that promotes or targets a set of osteolysis and/or osteoinduction regions. These regions can be changed, wherein in the second state, a second stimulation profile promotes or targets a second set of osteolysis and/or osteoinduction regions, wherein the first and second regions are not the same. Updating the electrical stimulation can involve changing the electrode polarity state, changing the current magnitude of a particular electrode, transitioning an electrode between an active state and an inactive state. Changing magnitude can include changing or adjusting current, voltage, impedance, signal pattern or other electrical property associated with electrode stimulation. For example, an electrode previously used as a cathode or anode may be turned off. Similarly, an electrode that was not utilized in driving electrical current can be activated, either as an anode or a cathode.

Block S240, which includes measuring impedance across the set of electrodes, functions to monitor bone growth. Measuring impedance preferably includes setting electrical state of at least two electrodes, measuring an impedance metric between the two electrodes. Such impedance testing is performed across a multiple sets of electrodes. The multiple sets of electrodes can be selected to provide impedance information in different regions. Performing impedance testing can additionally include generating an impedance profile, which may use the multiple impedance values to determine a mapping of impedance in the vicinity of the implantable component. Measuring impedance can be used to provide a snapshot of current impedance conditions. Such impedance conditions preferably correlate to bone growth. Additionally measuring impedance can involve tracking impedance profiles over time such that the rate of osteolysis and osteoinduction can be tracked. The changes in bone growth could additionally be used to automatically drive stimulation, which may function to dynamically react to how a particular individual is reacting to the electrical stimulation.

The controlled electrical stimulation of Block S230 and monitoring of bone growth through Block S240 are preferably used cooperatively to adapt to various bone growth conditions and to dynamically guide bone growth according particular health objectives.

As shown in the simulated depiction of the fusion space around a spinal cage during stimulation of FIG. 25, during unfocused, uncontrolled stimulation and osteoinduction may cause heterotopic ossification, which may result in the creation of anterior osteophyte and/or damage to spinal code and spinal nerves. Additionally, as shown in FIG. 25, such effects can be dose dependent where larger stimulation amplitudes can result in more osteoinduction, but may also lead to higher risks of uncontrolled dangerous heterotopic ossification during non-focused, non-guided osteoinduction.

The method can address such effects through controlled and dynamic electrical stimulation. The onset of such ossification patterns may be detected prior to reaching a critical situation, and the electrical stimulation can be adjusted to promote a counteracting stimulation profile. As shown in FIG. 26, it may be possible to select which region within the fusion space undergoes osteoinduction and osteolysis thus sculpting bone formation during stimulation through the method and/or system. The stimulation configuration can set a plurality of electrodes as cathodes, anodes or passive sites create regions of osteoinduction and osteolysis which may be used to dynamically sculpt desired bone growth and prevent and/or correct various scenarios of heterotopic ossification. Scenarios of guided osteoinduction can include managing mass formations in the spinal canal, managing mass formations in the spinal canal and intervertebral foramen, managing uni-lateral anterior osteophytes, managing unilateral anterior osteophytes and bilateral posterior osteophytes, increasing bone mass on one or both sides of fusion space, and/or other scenarios of guided osteoinduction.

Managing mass formation in the spinal canal can function to promote osteolysis in the spinal canal while maintaining osteoinduction the rest of the fusion space by sourcing current from electrode sites connected to end stage 412 while sinking current into electrode sites connected to remaining end stages.

Managing mass formation in the spinal canal and (unilateral) intervertebral foramen can function to promote osteolysis in the spinal canal and unilaterally in one of the intervertebral foramen while maintaining osteoinduction in the rest of the fusion space by sourcing current from electrode sites connected to end stages 412 and 411 while sinking current into electrode sites connected to remaining end stages.

Managing unilateral anterior osteophytes can function to promote osteolysis unilaterally in the anterior vertebral body while maintaining osteoinduction the rest of the fusion space by sourcing current from electrode sites connected to end stage 415 while sinking current into electrode sites connected to remaining end stages.

Managing unilateral anterior osteophytes and bilateral posterior osteophytes can function to promote osteolysis unilaterally in the anterior vertebral body and bilaterally in the posterior vertebral body while maintaining osteoinduction the rest of the fusion space by sourcing current from electrode sites connected to end stages 412 and 415 while sinking current into electrode sites connected to remaining end stages.

Increasing bone mass on one or both sides of the fusion space while maintaining current fusion mass in the anterior fusion space to avoid the creation of anterior osteophytes can function to promote osteolysis in the spinal canal, osteoinduction on both sides of the fusion space and neither osteolysis nor osteoinduction in the anterior of the fusion space by sourcing current from electrodes sites connected to end stages 412 while sinking current into electrode sites connected to end stages 411, 415, 413, and 414 (while electrodes connected remaining end stages neither sourced or sinked current).

Figure 27:
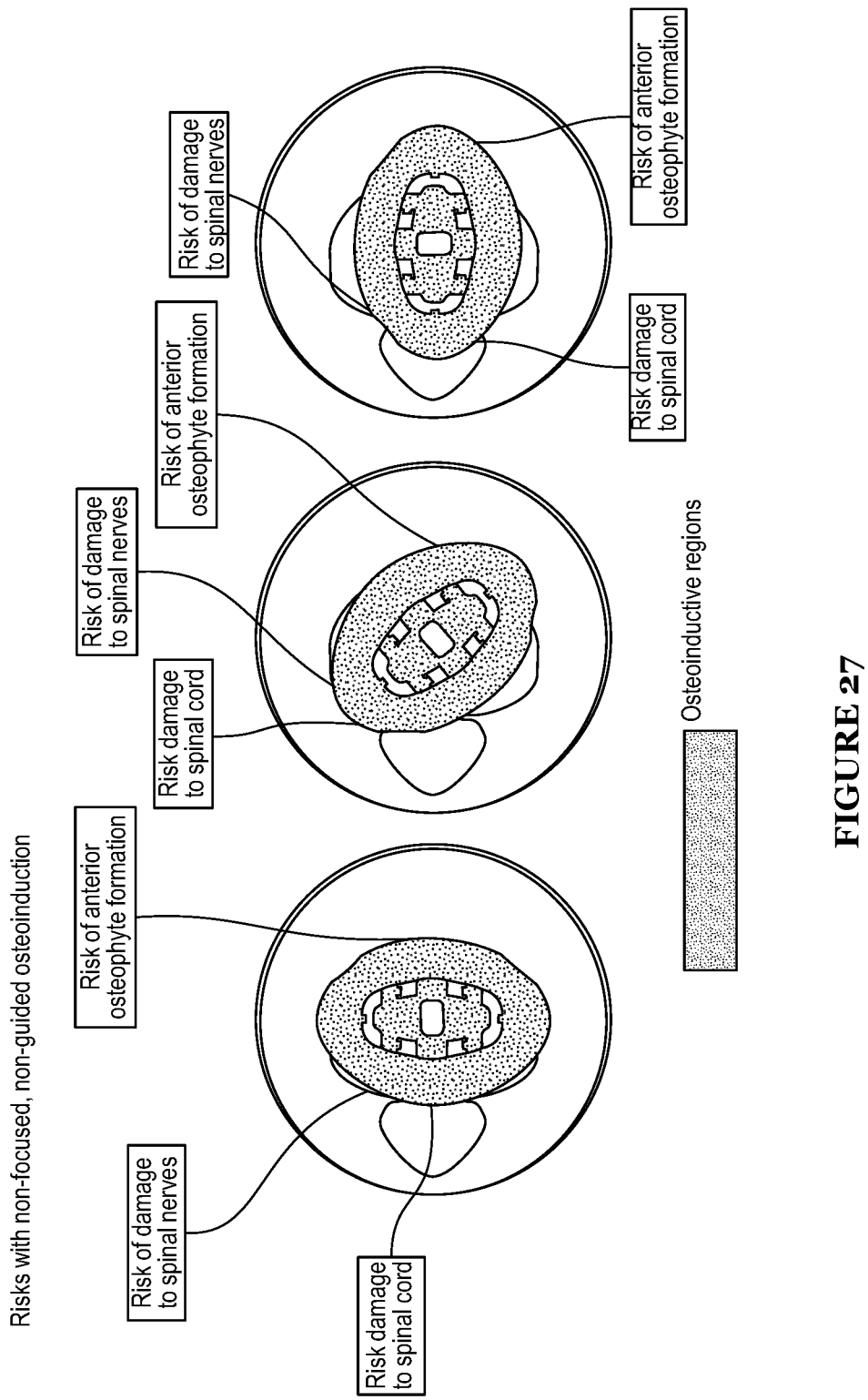
FIG. 27 shows osteoinductive regions within the fusion space during stimulation for different placements of the implantable component(s) using one embodiment.

As shown in the stimulated depiction of the fusion space around a spinal cage of FIG. 27, non-focused, non-guided osteoinduction may additionally result in heterotopic ossification resulting in the creation of anterior osteophytes, damage to spinal cord, and/or spinal nerves for various placement angles of a spinal cage (as indicated by the three angles of 0 degrees, 45 degrees and 90 degrees in FIG. 27).

FIGS. 28A-C show how may be possible to select which region within the fusion space undergoes osteoinduction and osteolysis thus sculpting bone formation during stimulation using the method and/or system and that such use of the method and system can be resilient to implant placement angle (e.g., is not sufficiently sensitive to implant placement angle). Such implant placement resilience can additionally be maintained in various scenarios of guided osteoinduction.

For example, embodiment 420 can be used in managing pathological bone or preventing mass formation in the spinal canal. Embodiment 420 can be used to ensure osteolysis in the spinal canal while maintaining osteoinduction the rest of the fusion space regardless of placement angle. For the three different placement angles (o, 45, and 90 degrees, FIGS. 28 A, B, and C) this may be achieved by sourcing current from electrode sites connected to end stages 421, 421/428/427, and 427 for the three different placement angles, while, for each placement angle, sinking current into electrode sites connected to remaining end stages.

In another example, embodiment 420 can be used in managing or preventing mass formation in the spinal canal and (unilateral) intervertebral foramen. Embodiment 420 can be used to ensure osteolysis in the spinal canal and unilaterally in one of the intervertebral foramen while maintaining osteoinduction the rest of the fusion space regardless of implant placement angle. For the three different placement angles (o, 45, and 90 degrees, FIGS. 14 A, B, and C) this can be achieved by sourcing current from electrode sites connected to end stages 421/428, 428/427, and 427/426 for the three different placement angles, while, for each placement angle, sinking current into electrode sites connected to remaining end stages.

In another example, embodiment 420 can be used in managing or preventing unilateral anterior osteophytes. Embodiment 420 can be used to ensure osteolysis unilaterally in the anterior vertebral body while maintaining osteoinduction the rest of the fusion space regardless of placement angle. For the three different placement angles (0, 45, and 90 degrees, FIGS. 28 A, B, and C) this can be achieved by sourcing current from electrode sites connected to end stages 427/426, 426/425, and 425/424 for the three different placement angles, while, for each placement angle, sinking current into electrode sites connected to remaining end stages.

In another example, embodiment 420 can be used in managing or preventing unilateral anterior osteophytes and bilateral posterior osteophytes. Embodiment 420 can be used to ensure osteolysis unilaterally in the anterior vertebral body and bilaterally in the posterior vertebral body while maintaining osteoinduction the rest of the fusion space regardless of placement angle. For the three different placement angles (0, 45, and 90 degrees, FIGS. 28 A, B, and C) this can be achieved by sourcing current from electrode sites connected to end stages 421/426, 428/426/425, and 427/425/424 for the three different placement angles, while, for each placement angle, sinking current into electrode sites connected to remaining end stages.

In yet another example, embodiment 420 can be used in increasing bone mass on one or both sides of the fusion space while maintaining current fusion mass in the anterior fusion space to avoid the creation of anterior osteophytes. Embodiment 420 can be used to ensure osteolysis in the spinal canal, osteoinduction on both sides of the fusion space, or neither osteolysis nor osteoinduction in the anterior of the fusion space regardless of placement angle. For the three different placement angles (0, 45, and 90 degrees, FIGS. 28A, B, and C) this can be achieved by sourcing current from electrode sites connected to end stages 421, 428/427, and 427, sinking current into electrode sites connected to end stages 428/427/422/423, 426/425/421/422, and 428/421/426/425 (for each placement angle, electrodes connected to remaining end stages were neither sourcing or sinking current).

Other suitable embodiments may similarly be used to address implant placement resilience.

Block S250, which includes communicating with at least one non-implantable device functions to send and/or receive data from an outside device. A non-implantable device may send communication messages or data to the implantable device. Such communications can be input used in determining the operating state of the implantable device. In one variation, communicating can include transmitting operational directives through the power signal, but the non-implantable device may alternatively communicate with the implantable device in any suitable manner. Accordingly, the implantable device is operable for receiving operational directives at the implantable component. The implant circuitry can be configured to decode or otherwise interpret the communicated messages and then respond appropriately. The inbound messages to the implantable device can specify stimulation settings, operational logic, data requests, diagnostics request, and/or any suitable directive or information. The stimulation settings can be used in setting the stimulation profile and determining how the electrodes are stimulated.

Communicating with at least one non-implantable device can additionally include transmitting data to the non-implantable device. Outbound communication can include impedance profile or measurement data, operating status (e.g., current stimulation conditions), diagnostics reports (e.g., power status, electrode status, etc.), and/or any suitable information.

Inbound and outbound communication may be executed over the same communication channel/medium, but communication may alternatively use two or more mediums. For example, inbound communication may use the wirelessly transmitted power signal and outbound communication may use low energy Bluetooth or an alternative medium of communication. In one variation, the communication can be encrypted or otherwise secured. Secured communication may function to prevent malicious data requests or illicit directives. In one implementation, an implantable component may be registered to a particular non-implantable component The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for electrical stimulation by a spinal cage implantable medical device comprising:
   providing at least one implantable component that includes a set of electrodes with at least three electrodes and implant circuitry used in electrically interacting with a fusion region of the implantable component, each electrode of the set of electrodes is: integrated into a body of the implant component, conductively coupled to the implant circuitry, and conductively isolated from each other electrodes of the set of electrodes;
   electrically stimulating the set of electrodes which comprises independently controlling a stimulation state of each electrode of the set of electrodes according to a first stimulation profile thereby promoting bone growth in a first region of the fusion region;
   generating, by measuring multiple impedance values between different sets of electrodes of the set of electrodes, an impedance profile; and
   in response to the impedance profile, updating electrical stimulation of the set of electrodes which comprises updating stimulation states of at least a subset of the set of electrodes according to a second stimulation profile thereby changing promotion of bone growth to a second region of the fusion region.

2. The method of claim 1, wherein updating the electrical stimulation of the set of electrodes comprises individually updating a polarity state and magnitude of a second subset of the set of electrodes.

3. The method of claim 2, wherein updating the electrical stimulation of the set of electrodes comprises updating a polarity of a first electrode and the magnitude of the electrical current flowing through the first electrode based in part on the impedance profile.

4. The method of claim 2, further comprising receiving at the implant circuitry an operating directive from a non-implantable component; wherein updating the electrical stimulation of the electrodes is updated based in part on the operating directive.

5. The method of claim 2, wherein updating the electrical stimulation of the set of electrodes is updated automatically based in part on the impedance profile.

6. The method of claim 1, further comprising communication with at least one non-implantable device, which comprises transmitting measured impedance information, wherein communicating with the at least one non-implantable device comprises transmitting power status; and at the non-implantable device transmitting a wireless energy signal receivable by implantable component and generated based in part on the transmitted power status.

7. The method of claim 1, wherein the first stimulation profile promotes a first region of osteolysis and a first region of osteoinduction.

8. The method of claim 7, further comprising, updating the electrical stimulation of the electrodes to a second stimulation profile, wherein activation state of each electrode of the set of electrodes is different between the first stimulation profile and the second stimulation profile such that the second stimulation profile promotes a second region of osteolysis and a second region of osteoinduction; wherein the first region of osteolysis is different from the second region of osteolysis and the first region of osteoinduction is different from the second region of osteoinduction.

9. The method of claim 1, wherein measuring impedance values between different sets of electrodes comprises, for multiple groups of electrodes of the set of electrodes, independently setting an electrical state of a group of electrodes and measuring impedance value between the group of electrodes.

10. The method of claim 1, tracking impedance profiles over time and tracking rate of bone growth.

11. The method of claim 1, wherein controlling a stimulation state of each electrode of the set of electrodes according to a first stimulation profile comprises, according to the first stimulation profile, setting a first set of electrodes with an active stimulation state; and wherein updating the electrical stimulation the set of electrodes comprises, according to the second stimulation profile, setting a second set of active electrodes, which is different from the first set of electrodes, with an active stimulation state.

12. The method of claim 1, wherein at least one electrode of the set of electrodes has an active stimulation state in the first stimulation profile and has an inactive stimulation state in the second stimulation profile.

13. The method of claim 1, wherein at least one electrode of the set of electrodes has an inactive stimulation state in the first stimulation profile and has an active stimulation state in the second stimulation profile.

14. The method of claim 1, wherein updating the electrical stimulation of the set of electrodes comprises, updating a first electrode of the set of electrodes from sourcing current in the first stimulation profile to sinking current according to the second stimulation profile.

15. The method of claim 1, wherein updating the electrical stimulation of the set of electrodes comprises, updating a first electrode of the set of electrodes from sinking current in the first stimulation profile to sourcing current according to the second stimulation profile.

* * * * *